United States Patent [19]

Fujiwhara et al.

[11] 4,155,765
[45] May 22, 1979

[54] COLOR PHOTOGRAPHIC MATERIALS CONTAINING AGENTS FOR PREVENTING DYE IMAGES FROM FADING

[75] Inventors: Mitsuto Fujiwhara; Takashi Sasaki; Takashi Uchida, all of Hino, Japan

[73] Assignee: Konishiroku Photo Industry Co., Ltd., Tokyo, Japan

[21] Appl. No.: 819,813

[22] Filed: Jul. 28, 1977

[30] Foreign Application Priority Data

Jul. 31, 1976 [JP] Japan .................................. 51-91917

[51] Int. Cl.$^2$ ................................................ G03C 1/76
[52] U.S. Cl. .......................................... 96/74; 96/56; 96/77; 96/100 R
[58] Field of Search ........................ 96/100, 56, 95, 77

[56] References Cited
U.S. PATENT DOCUMENTS

| 3,574,627 | 4/1971 | Stern et al. ............................. 96/100 |
| 3,930,866 | 1/1976 | Oishi et al. .............................. 96/56 |
| 4,015,990 | 4/1977 | Ishida et al. ............................ 96/56 |

Primary Examiner—J. Travis Brown
Attorney, Agent, or Firm—Bierman & Bierman

[57] ABSTRACT

This invention involves a color photographic material which contains a support and a hydrophilic layer containing a dye image wherein the material contains a compound represented by the following formula:

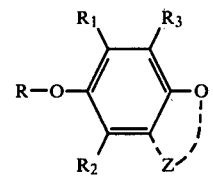

wherein R represents an alkyl group, an alkenyl group, a cycloalkyl group, an aryl group or a heterocyclic ring; $R_1$, $R_2$ and $R_3$ individually represent hydrogen, halogen, an alkyl group, an alkylthio group, an alkoxy group, an aryl group, an aryloxy group, an arylthio group, an acyl group, an acylamino group, a diacylamino group, an acyloxy group, a sulfonamido group, an alkylamino group, a cycloalkyl group or an alkoxycarbonyl group; and Z represents an atomic group or groups necessary for forming a chroman or coumaran ring; provided that R and $R_1$ can cooperatively be cyclized to form a chroman or coumaran ring.

17 Claims, No Drawings

COLOR PHOTOGRAPHIC MATERIALS CONTAINING AGENTS FOR PREVENTING DYE IMAGES FROM FADING

This invention relates to color photographic materials and particularly to color photographic materials in which a dye image obtained by processing a silver halide color photosensitive material has been prevented from discoloring, fading and yellow staining owing to light.

It is known that a silver halide color photosensitive material is processed by use of an aromatic primary amine compound to develop an imagewise exposed silver halide photosensitive material and a dye image is formed by reaction of an oxidation product of amine with a coupler, thereby to obtain a color image.

In forming a cyan, magenta or yellow dye image according to the process mentioned above, there is usually employed a phenol or naphthol type coupler, a 5-pyrazolone, pyrazolinobenzimidazole, pyrazolotriazole, indazolone or cyanoacetyl type coupler, or an acylacetamide or dibenzoylmethane type coupler.

The dye images obtained in this manner are desired not to fade even when they are exposed to light for a long period of time or stored under such circumstances as at high temperature and high humidity. It is well known, however, that the dye images thus formed are not found yet satisfactory in fastness to light, mainly ultraviolet or visible light and easily discolor, fade and yellow-stain when subjected to exposure to these active rays. In order to eliminate such drawbacks, there have heretofore been proposed a process using selected couplers less in fading property, a process using ultraviolet absorbers to protect a dye image from an ultraviolet light exposure, or a process using agents for preventing a dye image from fading due to light.

For instance, there have heretofore been proposed various processes in which a color photographic material is incorporated with an ultraviolet absorber to enhance light fastness of a dye image formed thereon. In order to impart satisfactorily light fastness to the resulting dye image by the use of an ultraviolet absorber, however, it becomes necessary to use a relatively large amount of the ultraviolet absorber for attaining the object. In this case, there was frequently observed such phenomenon that the resulting dye image had been markedly stained due to color of the ultraviolet absorber itself. In addition, even the use of an ultraviolet absorber does not produce any effect on prevention of the resulting dye image from fading due to a visible light exposure, and thus there was a limit to enhancement of light fastness of the resulting dye image by the use of the ultraviolet absorber. Further, there have been proposed use of agents for prevention of fading, which agents have phenolic hydroxyl groups or such groups as these forming phenolic hydroxyl groups on hydrolysis. For example, Japanese Patent Publications Nos. 31256/1973 and 31625/1973 disclose bisphenols, U.S. Pat. Nos. 2,369,262 and 4,015,990 disclose α-tocopherols and their acyl derivatives, U.S. Pat. Nos. 3,432,300 and 3,574,627 disclose 6-hydroxychromanes, U.S. Pat. No. 3,573,050 discloses 5-hydroxycoumaran derivatives, and Japanese Patent Publication No. 20977/1974 discloses 6,6'-dihydroxy-2,2'-bisspirochromanes.

Actually, however, the above-mentioned compounds are not found yet sufficiently satisfactory for attaining the object. Although they certainly show an effect on improvement of light fastness of dyes, the improvement is not sufficient in addition that some of them come to show a sudden reduction or disappearance of their effect on prevention of fading at a certain point of time during long term storage of color photographic materials. Furthermore, in some cases, the so-called after-yellowing (hereinafter called "Y-stain") owing to ultraviolet light is brought about in the portions of the processed color photographic material where unreacted couplers remain, i.e. unexposed areas of the material. Some of them are found small in solubility in solvents used for incorporation into a color photosensitive material of the same. Because of low resistance to diffusion, some of them come to diffuse into a processing solution having a high pH. Certain kinds of these compounds are relatively excellent in their effect on prevention of fading of a dye image obtained from a magenta coupler but have no effect on prevention of fading of a dye image obtained from a yellow or cyan coupler, and some of these compounds promote fading of the resulting dye image contrary to expectation.

An object of the present invention is to provide color photographic materials containing agents for prevention of fading which agents are excellent in their effect on prevention of fading, in solubility in high boiling solvents and the like, in dispersion stability, in resistance to diffusion, have no adverse effect on other photographic additives and also do not hinder couplers from color development.

The present inventors have found as a result of extensive researches that the above-mentioned object of the present invention can be accomplished by incorporating at least one of the compounds represented by the following general formula [I] (hereinafter referred to as "the present compounds") into color photographic materials:

General formula [I]

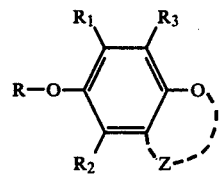

In the general formula [I], R represents an alkyl group, an alkenyl group, a cycloalkyl group, an aryl group or a heterocyclic ring; $R_1$, $R_2$ and $R_3$ individually represent hydrogen or halogen, or an alkyl group, an alkylthio group, an alkoxy group, an aryl group, an aryloxy group, an arylthio group, an acyl group, an acylamino group, a diacylamino group, an acyloxy group, a sulfonamido group, an alkylamino group, a cycloalkyl group or an alkoxycarbonyl group; and Z represents an atomic group or groups necessary for forming a chromane or coumaran ring; and further R and $R_1$ may cooperatively by cyclized to form a chromane or coumaran ring; and said chromane or coumaran rings include a chromane or coumaran nucleus substituted with halogen, an alkyl group, an alkoxy group, an alkenyl group, an alkenyloxy group, an aryl group, an aryloxy group, N-substituted amino or a heterocyclic ring or an atomic group or groups for forming a condensed-ring containing said chromane or coumaran nucleus.

Each of the above groups or rings includes the substituted, so that, for example, the alkyl group includes substituted or unsubstituted alkyl, the aryl group includes substituted or unsubstituted aryl, and the alkenyl group includes substituted or unsubstituted alkenyl. The same is true as to the rest of the groups or rings.

Among the compounds represented by general formula [I], those which are especially of usefulness in the present invention are compounds represented by the following general formulas [II], [III] and [IV] respectively as mentioned below:

General formula [II]

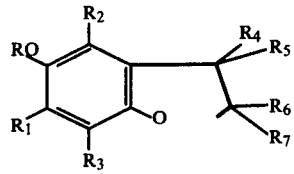

General formula [III]

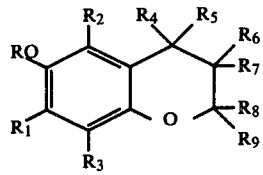

General formula [IV]

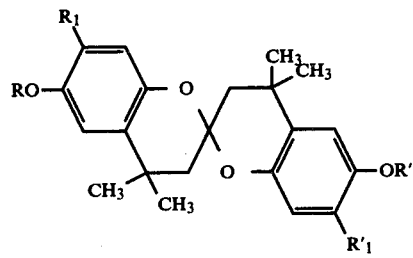

In general formulas [II], [III] and [IV], R, $R_1$, $R_2$ and $R_3$ are individually as defined in general formula [I]; R' is as defined for R in general formula [I]; $R'_1$ is as defined for $R_1$ in general formula [I] (R and R' may be the same or different and $R_1$ and $R'_1$ may be the same or different); and $R_4$, $R_5$, $R_6$, $R_7$, $R_8$ and $R_9$ individually represent hydrogen, an alkyl group, an alkyloxy group, an alkylthio group, an alkenyl group, an alkenyloxy group, an aryl group an aryloxy group, an N-substituted amino group or a heterocyclic ring; and $R_8$ and $R_9$ may cooperatively be cyclized to form a hydrocarbon ring which includes a hydrocarbon ring nucleus unsubstituted or substituted with an alkyl group, the hydrocarbon ring being such as a cyclohexane ring. As same as explained in general formula [I], all the groups and rings in general formulas [II], [III] and [IV] include the unsubstituted or the substituted.

Particularly useful among the compounds represented by general formulas [II], [III] and [IV] in the present invention, are those in which R and R' are individually substituted or unsubstituted alkyl or cycloalkyl, $R_1$, $R'_1$, $R_2$ and $R_3$ are individually hydrogen, alkyl or cycloalkyl more preferablly $R_3$ is hydrogen, at least one of the $R_2$ and $R_1$ or $R'_1$ is lower alkyl especially methyl, $R_4$, $R_5$, $R_6$, $R_7$, $R_8$ and $R_9$ are individually hydrogen or halogen, alkyl or cycloalkyl, and R and $R_1$ are cooperatively cyclized to form the chromane ring and $R_8$ and $R_9$ are cooperatively cyclized to form the hydrocarbon ring. In general formula [III], preferably R is an alkyl group having 8-32 carbon atoms, the group including substituted or unsubstituted alkyl. More preferablly the present compounds are those represented by general formulas [IV] and [III] in which general formula [III] R is the alkyl group of 8-32 carbon atoms.

Of the compounds represented by the general formula [I], those which are of usefulness in the present invention include also compounds represented by the following general formula [V].

General formula [V]

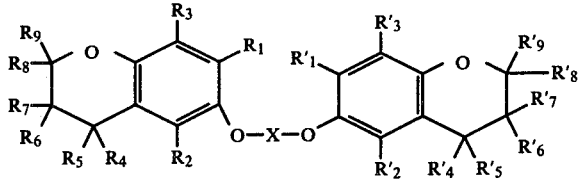

In the general formula [V], $R_1$, $R_2$ and $R_3$ are individually as defined in the aforementioned general formula [I]; and $R'_1$, $R'_2$ and $R'_3$ are respectively as defined for $R_1$, $R_2$ and $R_3$.

$R_4$, $R_5$, $R_6$, $R_7$, $R_8$ and $R_9$ are individually as defined in the aforementioned general formula [I], $R'_4$, $R'_5$, $R'_6$, $R'_7$, $R'_8$ and $R'_9$ are respectively as defined for $R_4$, $R_5$, $R_6$, $R_7$, $R_8$ and $R_9$; and X represents an alkylene group, a phenylene group, a cycloalkylene group or a divalent heterocyclic group. A carbon chain in the alkylene group may contain —O—, —S—, —NH— and/or —$SO_2$— therein as a chain member or members. As same as explained before, the above groups include the substituted and the unsubstituted.

Particularly useful among the compounds represented by general formula [V] in the present invention, are those in which $R_1$ and $R'_1$ are individually an alkyl group; $R_2$, $R'_2$, $R_3$ and $R'_3$ are individually hydrogen, $R_5$, $R'_5$, $R_6$, $R'_6$, $R_7$ and $R'_7$ are individually hydrogen and X is alkylene or alkylene in which a carbon chain in the alkylene may be separated by —$SO_2$—.

In this invention, preferablly the alkyl and alkenyl groups except for R in general formula [III] have 1-32 carbon atoms and the heterocyclic rings and divalent heterocyclic group are of the 5- or 6- membered such as those derived from piperadine, morpholine, imidazoline, thiazoline, pyridine, pyrimidine, triazine, etc.

The groups and rings appeared in all the general formulas include the substituted as explained before. Although the substituents may be any substituents, preferred ones are one or more appropriately selected from the group consisting of halogen, cyano, hydroxy, amino, nitro, sulfo, carboxy, an alkyl group, an alkenyl group, an aryl group, a cycloalkyl group, an alkoxy group, an alkenyloxy group, an aryloxy group, acyl, acyloxy, oxycarbonyl, an acylamino group, a carbamoyl group, a sulfonamido group, a sulfamoyl group, a heterocyclic ring and mono- or di-alkylamino among which halogen, cyano, hydroxy, amino, an alkyl group, an aryl group, oxycarbonyl and mono- or di-alkylamino are more preferred.

Typical examples of the above-mentioned compounds are shown below, but the present compounds are not limited thereto.

(1) 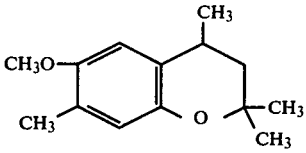 b.p. 130°–5° C./ 0.2 mmHg (2) 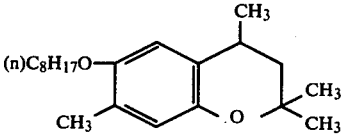 b.p. 152°–3° C./ 0.1 mmHg (3) 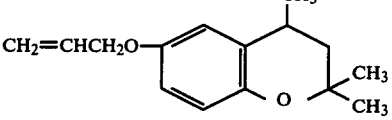 b.p. 125°–135° C./ 0.1 mmHg (4) 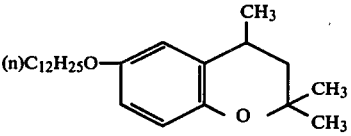 b.p. 175°–7° C./ 0.1 mmHg (5) 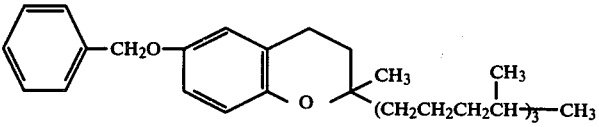 b.p. 130°–140° C./ 0.001 mmHg (6) 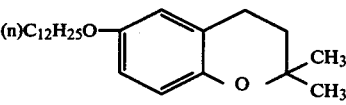 b.p. 255°–260° C./ 5 mmHg (7) 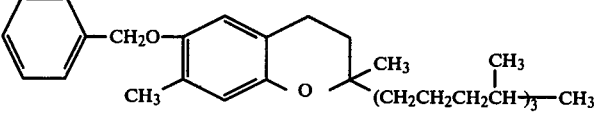 b.p. 210°–220° C./ 0.02 mmHg (8) 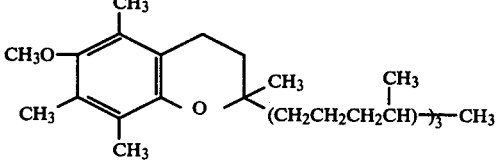 b.p. 190°–210° C./ 0.03 mmHg (9) 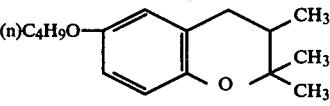 b.p. 142°–5° C./ 0.3 mm Hg

(10) 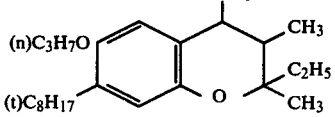 m.p. about 30°–35° C.

(11) 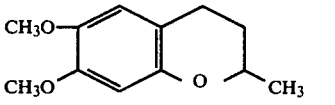 m.p. 41°–8° C.

(12) 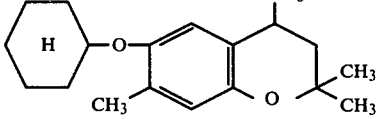 b.p. 180°–5° C./ 2 mmHg

-continued

| | | |
|---|---|---|
| (13) | [structure: 4-phenoxy substituted chroman with 2,2-dimethyl and 4-methyl] | m.p. 93°–5° C. |
| (14) | [structure: 6-methoxy-7,8-dimethyl-2,2-dimethylchroman] | m.p. 59°–60° C. |
| (15) | [structure: KOOCCH₂O- and (t)C₄H₉-substituted 2,2-dimethyl-4-methylchroman] | m.p. >280° C. |
| (16) | [structure: (n)C₈H₁₇OOCCH₂CH₂O-substituted 2,2-dimethyl-4-isopropylchroman] | m.p. about 30°–40° C. |
| (17) | [structure: guanidino-imino ether substituted chroman] | m.p. >280° C. |
| (18) | [structure: (n)C₃H₇O-, cyclohexyl-substituted 2,2,3,3-tetramethylbenzofuran] | b.p. 130°–137° C./ 0.03 mmHg |
| (19) | [structure: CH₃O-, CH₃-substituted 3,3-dimethyl-2-ethoxybenzofuran] | b.p. 121°–8° C./ 0.1 mmHg |
| (20) | [structure: CH₃O-, (t)C₈H₁₇-substituted 3,3-dimethyl-2-piperidinylbenzofuran] | m.p. 103°–6° C. |
| (21) | [structure: (i)C₅H₁₁O-, (t)C₄H₉-substituted 3,3-dimethyl-2-morpholinylbenzofuran] | b.p. 131°–3° C./ 0.01 mmHg |
| (22) | [structure: C₂H₅O-, (n)C₁₈H₃₇-substituted spiro chroman-cyclohexane with gem-dimethyl] | m.p. 100°–110° C. |
| (23) | [structure: CH₃O-substituted 3,4-dichloro-2,2-dimethylchroman] | m.p. 52°–3° C. |

-continued
(24) 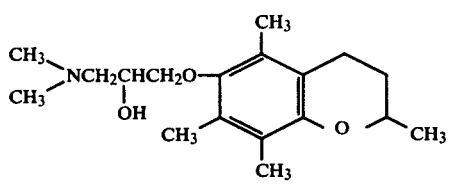 m.p. 113°–9° C.
(25) 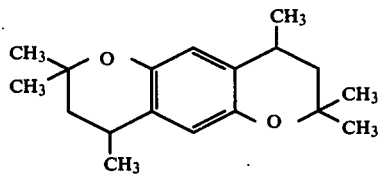 m.p. 173°–5° C.
(26) 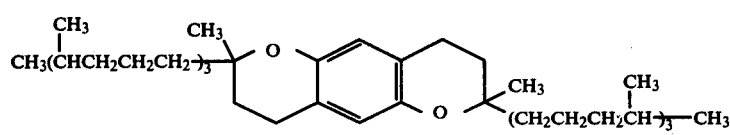 b.p. 270°–300° C./ 0.05 mmHg
(27) 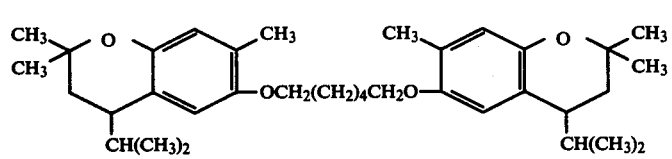 Viscous liquid
(28) 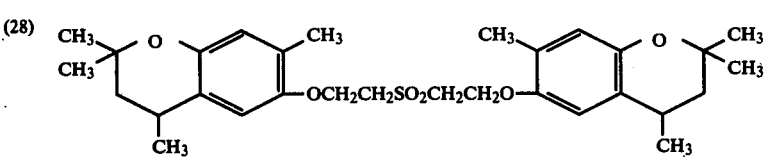 m.p. 85°–7° C.
(29) 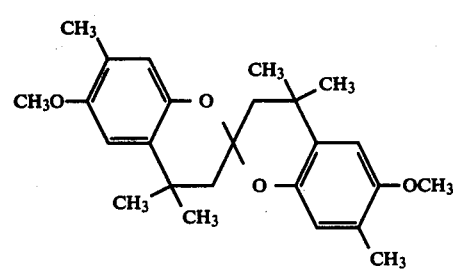 m.p. 182°–3° C.
(30) 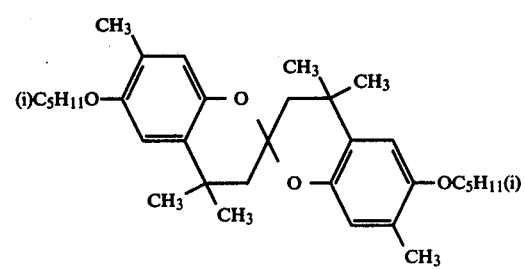 m.p. 99°–100° C.
(31) 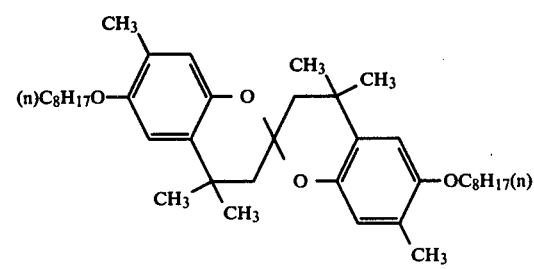 m.p. 93°–4° C.

-continued
(32) 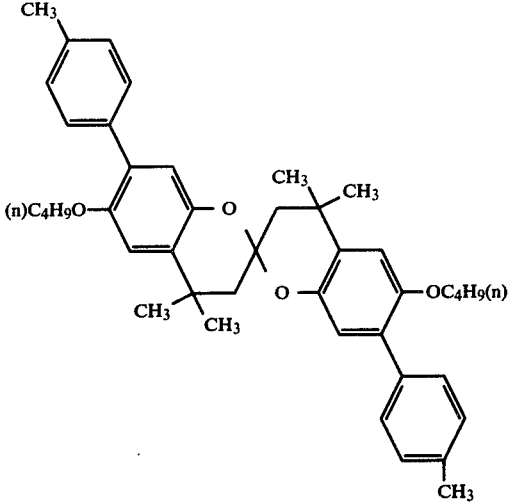 m.p. 193°–5° C.
(33) 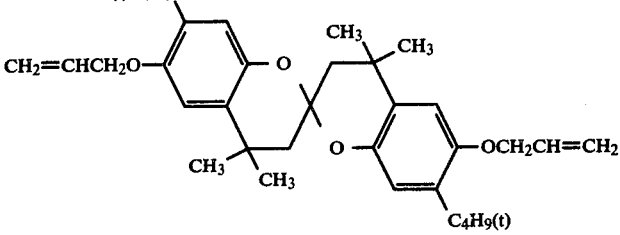 m.p. 150°–5° C.
(34) 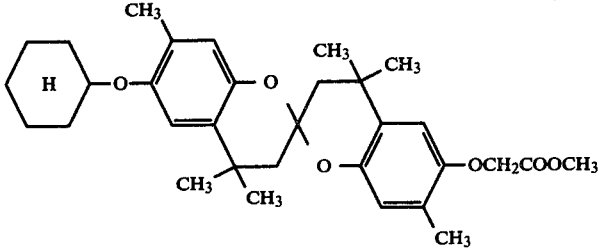 m.p. 140°–4° C.
(35) 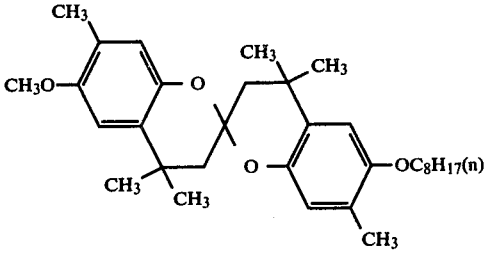 m.p. 94°–7° C.
(36) 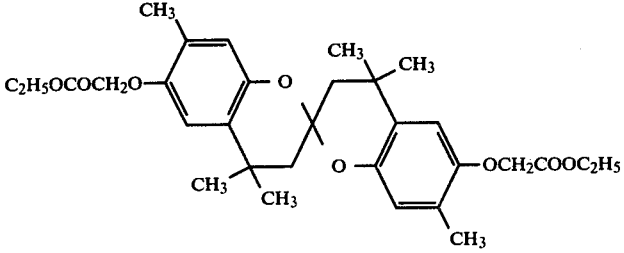 m.p. 115°–8° C.

(37) 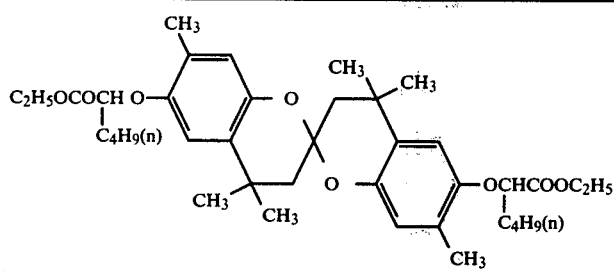 b.p. about 270°–280° C./ 0.3 mmHg
(38) 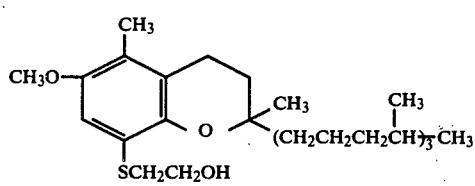 Viscous liquid
(39) 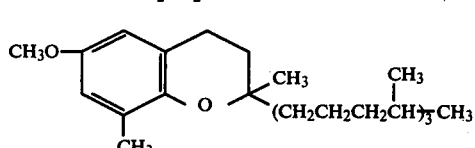 Viscous liquid
(40) 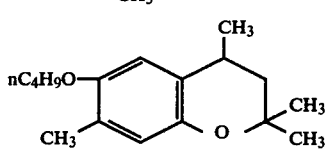 b.p. 143°–4° C./ 2 mmHg
(41) 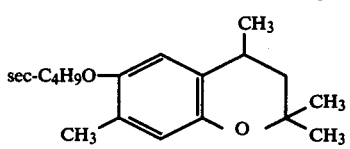 b.p. 116°–8° C./ 0.07 mmHg
(42) 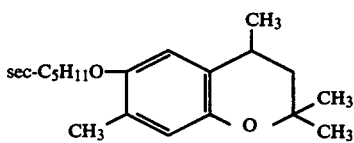 b.p. 125°–8° C./ 0.06 mmHg
(43) 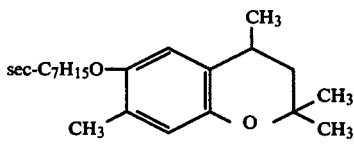 b.p. 145°–8° C./ 0.04 mmHg
(44) 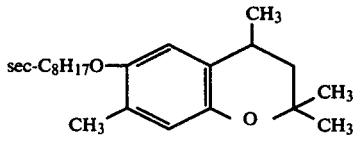 b.p. 143°–4° C./ 0.06 mmHg
(45) 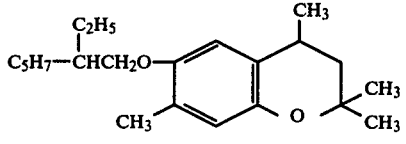 b.p. 144°–7.5° C./ 0.01 mmHg
(46) 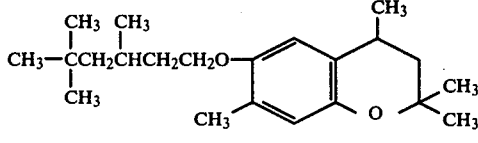 b.p. 153°–4° C./ 0.005 mmHg
(47) 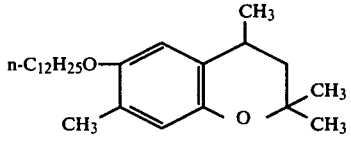 b.p. 188°–193° C./ 1 mmHg

| | Structure | Properties |
|---|---|---|
| (48) | n-C₁₆H₃₃O-[benzene with CH₃]-CH(CH₃)-CH₂-C(CH₃)₂-O (chroman) | b.p. 220°–223° C./ 2 mmHg |
| (49) | n-C₁₈H₃₇O-[benzene with CH₃]-CH(CH₃)-CH₂-C(CH₃)₂-O (chroman) | b.p. 230°–233° C./ 2 mmHg |
| (50) | NC(CH₂)₃O-[benzene with CH₃]-CH(CH₃)-CH₂-C(CH₃)₂-O (chroman) | m.p. 73°–4° C. |
| (51) | C₂H₅OOCCHO(C₄H₉)-[benzene with CH₃]-CH(CH₃)-CH₂-C(CH₃)₂-O (chroman) | b.p. 155°–160° C./ 0.008 mmHg |
| (52) | HOOCCHO(C₄H₉)-[benzene with CH₃]-CH(CH₃)-CH₂-C(CH₃)₂-O (chroman) | Viscous liquid |
| (53) | C₂H₅OOCCHO(n-C₁₂H₂₅)-[benzene with CH₃]-CH(CH₃)-CH₂-C(CH₃)₂-O (chroman) | b.p. 205°–210° C./ 0.002 mmHg |
| (54) | HOOCCHO(C₁₂H₂₅)-[benzene with CH₃]-CH(CH₃)-CH₂-C(CH₃)₂-O (chroman) | Colorless liquid (When purified by a column chromatograph.) |
| (55) | iso-C₃H₇O-[benzene]-CH₂-CH₂-C(CH₃)₂-O (chroman) | b.p. 122°–3° C./ 3 mmHg |
| (56) | sec-C₅H₇O-[benzene]-CH₂-CH₂-C(CH₃)₂-O (chroman) | b.p. 156°–9° C./ 4 mmHg |
| (57) | C₁₆H₃₃O-[benzene]-CH₂-CH₂-C(CH₃)₂-O (chroman) | m.p. 51°–51.5° C. |
| (58) | n-C₂₄H₅₀O-[benzene with CH₃]-CH(CH₃)-CH₂-C(CH₃)₂-O (chroman) | m.p. 54°–5° C. |
| (59) | n-C₃₀H₆₁O-[benzene with CH₃]-CH(CH₃)-CH₂-C(CH₃)₂-O (chroman) | m. 76°–8° C. |
| (60) | C₂H₅OOCCHO(C₆H₁₃)-[benzene with CH₃]-CH(CH₃)-CH₂-C(CH₃)₂-O (chroman) | b.p. 156°–159° C./ 0.003 mmHg |

-continued
(61) 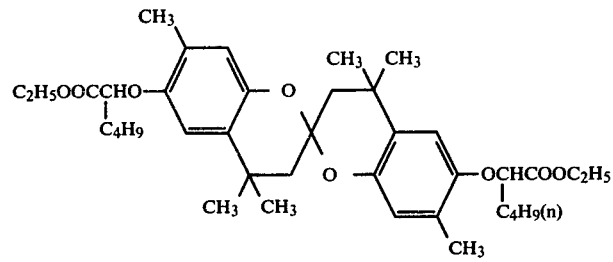 m.p. 55°–57° C.
(62) 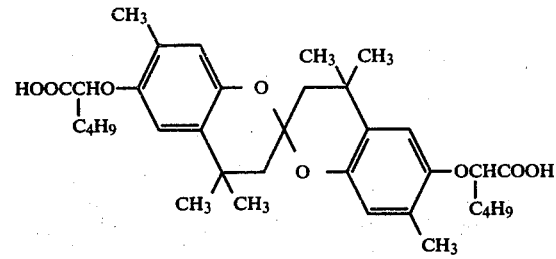 m.p. 153°–6° C.
(63) 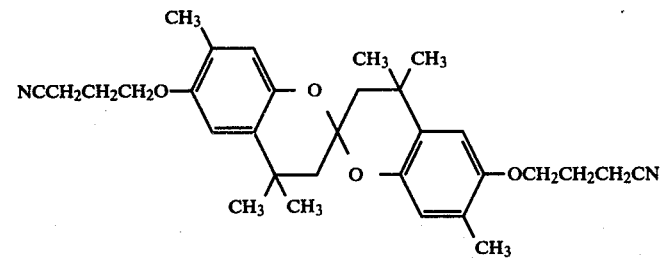 m.p.153°–4° C.
(64) 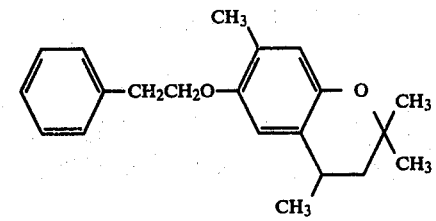 m.p. 75° C.
(65) 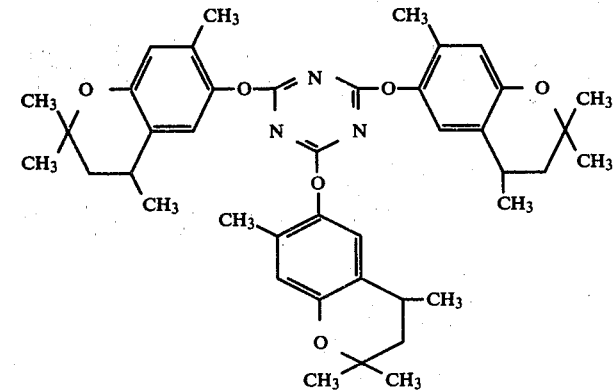 m.p. 197°–8° C.
(66) 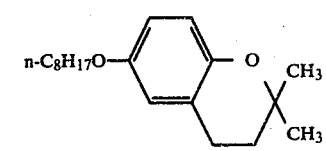 b.p. 173°–4.5° C./ 1.5 mmHg
(67) 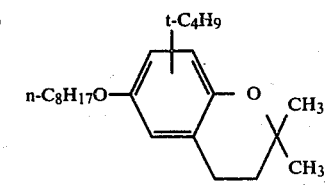 b.p. 187°–190° C./ 0.15 mmHg

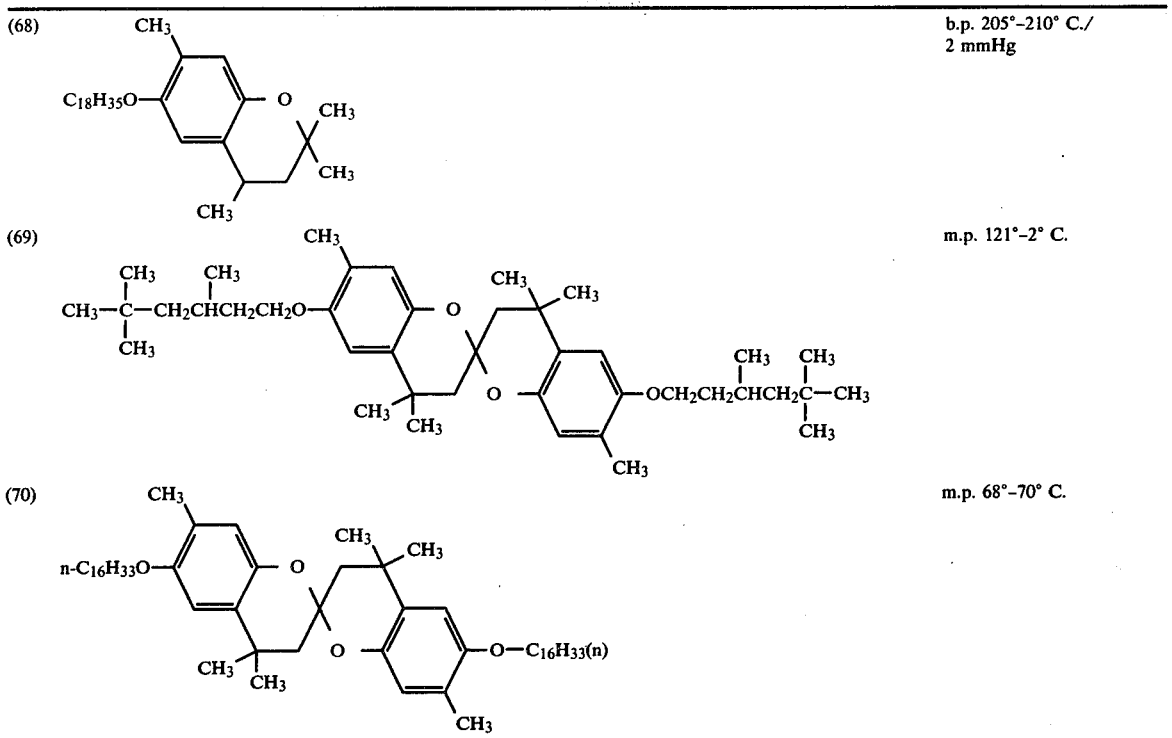

(68) b.p. 205°–210° C./2 mmHg

(69) m.p. 121°–2° C.

(70) m.p. 68°–70° C.

The present compounds may be prepared according to the following procedure: That is, 6-hydroxychromane, 5-hydroxycoumaran or 6,6'-dihydroxy-2,2'-bis-spirochromanes obtained according to processes disclosed in the aforementioned U.S. Pat. Nos. 3,432,300, 3,573,050, 3,574,627 and 3,764,337 are subjected to common alkylation wherein such compound is reacted in the presence of alkali with a halide, sulfuric esters or a vinyl compound, or alternatively such compound is combined, according to process disclosed in German Pat. No. 1,938,672, Journal of the American Chemical Society, Vol. 66, 1523–1525, and Journal of the Chemical Society, 1850–1852 (1958) and 3350–3378 (1959), with phenols having an ether bond at the p-position. Synthesis examples of the present compounds are shown below.

SYNTHESIS EXAMPLE 1

Synthesis of compound (2)

Into a solution of 206 g of 2,2,4,7-tetramethyl-6-chromanol and 193 g of n-octylbromide in 2 l of acetone is added 69 g of anhydrous potassium carbonate, and the resulting mixture is heated under reflux for 15 hours while stirring the mixture on a hot water bath. After completion of the reaction, inorganic substance formed thereby is separated by filtration and then the solvent is removed away. The residue is distilled under a reduced pressure to obtain 280 g of a viscous liquid, boiling point 152°–3° C./0.1 mm Hg.

Results of elementary analysis ($C_{21}H_{34}O_2$) Unit:%
Calculated: C: 79.25; H: 10.69. Found: C: 79.03; H: 10.82.

SYNTHESIS EXAMPLE 2

Synthesis of compound (5)

Into a solution of 2 g of p-benzyloxyphenol and 3 g of phytol in 25 ml of benzene is added 25 ml of formic acid, and the resulting solution is heated under reflux for 20 hours. The benzene layer is separated, washed with an aqueous alkali solution and then washed again with water and dried by use of anhydrous sodium sulfate, followed by concentration under a reduced pressure. The resulting residue is distilled under a reduced pressure, and a fraction having boiling point of 130°–140° C./0.001 mmHg is further purified by means of column chromatography to obtain 3.2 g of a viscous liquid.

Results of elementary analysis ($C_{33}H_{50}O_2$) Unit:%
Calculated: C: 82.85; H: 10.46. Found: C: 82.63; H: 10.54.

SYNTHESIS EXAMPLE 3

Synthesis of compound (31)

Into a solution of 184 g of 6,6'-dihydroxy-7,7'-dimethyl-4,4,4',4'-tetramethylbis-2,2'-spirochromane and 193 g of n-octylbromide in 1 l of ethanol is added 56 g of potassium hydroxide, and the resulting mixture is heated under reflux for 3 hours on an oil bath. After completion of the reaction, the deposited inorganic salt is separated by filtration and the solvent is removed away. The residue obtained is recrystallized from methanol to obtain 473 g of colorless crystals, melting point 93°–94° C.

Results of elementary analysis ($C_{39}H_{60}O_4$) Unit:%
Calculated: C: 79.05; H: 10.14. Found: C: 78.92; H: 10.31.

SYNTHESIS EXAMPLE 4

Synthesis of compound (40)

Into a mixed solution of 20.6 g of 2,2,4,7-tetramethyl-6-chromanol, 18.3 g of n-butylbromide and 200 ml of ethanol, is added 8.7 g of potassium hydroxide, and the resulting mixture is heated under reflux while stirring.

After completion of the reaction, an inorganic salt formed thereby is separated by filtration and then the solvent is removed away. The residue is distilled under a reduced pressure to obtain 26 g of a viscous liquid, boiling point 143°-4° C./2 mm Hg.

Results of elementary analysis ($C_{17}H_{26}O_2$) Unit:%
Calculated: C: 77.86; H: 9.92. Found: C: 77.59; H: 10.23.

SYNTHESIS EXAMPLE 5

Synthesis of compound (48)

A simular method as set forth above in synthesis example 4 is repeated using n-hexadecyl bromide in place of n-butyl bromide.

The residue is distilled under a reduced pressure to obtain a viscous liquid, boiling point 220°-223° C./2 mm Hg.

Results of elementary analysis ($C_{29}H_{50}O_2$) Unit:%
Calculated: C: 80.93; H: 11.63. Found: C: 81.00; H: 11.78.

SYNTHESIS EXAMPLE 6

Synthesis of compound (53)

A simular method as set forth in synthesis example 4 is repeated by use of ethyl α-bromomyristrate in place of n-butyl bromide. The residue is distilled under a reduced pressure to obtain a viscous liquid, boiling point 205°-210° C./0.002 mm Hg.

Results of elementary analysis ($C_{29}H_{48}O_4$) Unit:%
Calculated: C: 75.65; H: 10.43. Found: C: 75.42; H: 10.58.

SYNTHESIS EXAMPLE 7

Synthesis of compound (65)

20 g of potassium hydroxide is dessolved into 300 ml of ethanol. Into the resulting is added 2,2,4,7-tetramethyl-6-chromanol is refluxed for 30 minutes and thereafter ethanol is removed away. The residue is dissolved into 400 ml of benzene and thereinto is added 18.5 g of 2,4,6-trichloro-S-triazine. The resulting is heated under reflux. After completion of the reaction, as obtained inorganic substance is filtered away and the water liquid is concentrated under a reduced pressure to obtain crystals. The crystals are recrystalized by use of ethanol, so that needle-shaped crystals are obtained, melting point 197°-8° C.

Results of elementary analysis ($C_{42}H_{51}N_3O_6$) Unit:%
Calculated: C: 72.70; H: 7.41; N: 6.06. Found: C: 72.47; H: 7.31; N: 5.98.

SYNTHESIS EXAMPLE 8

Synthesis of compound (66)

Into a solution of 53.4 g of 2,2-dimethyl-6-chromanol and 75.3 g of n-dodecyl bromide in 200 ml of ethanol is added 25 g of potassium hydroxide, and the resulting mixture is heated under reflux for 2 hours. After completion of the reaction, inorganic compound formed thereby is separated by filtration and then the solvent is distilled off. The residue is distilled under reduced pressure to obtain 11 g of a viscous liquid, boiling point 173°-174.5° C./1.5 mm Hg.

Results of elementary analysis ($C_{19}H_{30}O_2$) Unit:%
Calculated: C: 78.62; H: 10.34. Found: C: 78.77; H: 10.23.

SYNTHESIS EXAMPLE 9

Synthesis of compound (67)

Into 5.8 g of compound (66) is added several drops of concentrated sulfuric acid and then isoprene is introduced thereinto for 3 hours while stirring. After reaction, into a reaction solution is added benzene to be dissolved. The solution is washed with water and dried by use of calcium chloride. After the solvent is removed away, the resulting residue is distilled under a reduced pressure to obtain 3.5 g of a viscous liquid of which boiling point is 187°-9° C./0.15 mm Hg. The compound is an isomeric mixture.

Results of elementary analysis ($C_{23}H_{38}O_2$) Unit:%
Calculated: C: 79.77; H: 10.98. Found: C: 79.90; H: 10.89.

The present compounds are desirably incorporated into a silver halide emulsion layer, but they may also be incorporated into other layers, for example, layers adjacent to the silver halide emulsion layer.

The present compounds which are oil-soluble are desirably incorporated, in general, according to methods disclosed in U.S. Pat. Nos. 2,322,027, 2,801,170, 2,801,171, 2,272,191 and 2,304,940, into a silver halide emulsion, by dissolving said compound together with a coupler in a high boiling solvent. If necessary, said high boiling solvent is used in combination with a low boiling solvent, and adding the resulting solution by dispersion into the silver halide emulsion. In this case, if necessary, hydroquinone derivatives, ultraviolet absorbers or known agent for prevention of fading may be used in combination therewith and a mixture of two or more compounds of the present invention may be employed. Now, the manner of incorporation into a silver halide emulsion of the present compounds is illustrated below in detail. One or two or more of the present compounds together with a coupler are dissolved (if necessary in combination with hydroquinone derivatives, ultraviolet absorbers or known agents for prevention of fading) into such high boiling solvent as organic acid amides, carbamates, esters, ketones and or urea derivatives, particularly di-n-butylphthalate, tricresyl phosphate, di-isooctylazelate, di-n-butylsebacate, tri-n-hexylsulfate, N,N-di-ethylcaprylamidobutyl, n-pentadecylphenyl ether and or fluoroparaffin, and/or if necessary, into such low boiling solvent as ethylacetate, butyl acetate, butyl propionate, cyclohexanol or cyclohexanetetrahydrofran (these high boiling and low boiling solvents may be used either singly or in the mixture thereof). The resulting solution is mixed with an aqueous solution comprising a hydrophilic binder, such as gelatin or the like, containing such anion type surface active agent and an alkylbenzenesulfonic acid or an alkylnaphthalenesulfonic acid and/or such nonionic surface active agent as sorbitane sesquioleate or sorbitanemonolaurate, the mixture is dispersed by emulsification by means of a high speed rotary mixer, a colloid mill or an ultrasonic wave dispersing apparatus, and the resulting dispersion is incorporated into a silver halide emulsion.

In the above case, if the coupler used is of a diffusible type, said coupler may be added into a color developer and an emulsified dispersion of the present compounds prepared in the above manner but not containing the coupler may be incorporated into the silver halide emulsion.

The present compounds produce a sufficient effect even when they are incorporated into a color photographic material obtained by processing a silver halide color photosensitive material by color development.

Because of substantial colorlessness, the amount of the present compounds to be incorporated is not particularly restricted. However, the presence in a silver halide color photosensitive material of the present compounds in an amount of about 15 g per mole of a dye formed by color development will suffice for the purpose of the present invention. Mainly from an economical reason, in the case of silver halide color photosensitive materials containing a coupler, it is preferred to use the present compounds in an amount of 5–300% by weight, preferably 10–100% by weight, based on the coupler used. In the case of silver halide color photosensitive materials containing no coupler, the amount of the present compounds to be incorporated is preferably 10–100 g, particularly 15–60 g, based on 1 mole of the silver halide present in the color photosensitive material.

As ultraviolet absorbers usable in combination with the present compounds, there may be mentioned, for example, thiazolidone, benzotriazole, acrylonitrile and benzophenone type compounds disclosed in U.S. Pat. Nos. 2,739,888, 3,004,896, 3,253,921, 3,533,794, 3,692,525, 3,705,805, 3,738,837, 3,754,919, 3,053,636 and 3,707,375 and British Pat. No. 1,321,355 and the like. The use of these compounds is of advantage in preventing the resulting dye image from fading due to a short wave actinic ray exposure, particularly the use, either singly or in combination, of Tinubin PS, Tinubin 320, Tinubin 326, Tinubin 327 and Tinubin 328 (products produced and sold by Chiba-Geigy) is of advantage.

Usable as dye image-forming couplers in silver halide color photographic materials according to the present invention, are those as disclosed in the undermentioned patents.

Of the dye image-forming couplers referred to the above, the yellow dye image-forming couplers are those of benzoylacetanilide and pivaloylacetanilide types, or 2 equivalent type yellow dye image-forming couplers in which the carbon atom at the coupling position has been substituted with a substituent (so-called split-off group) releasable at the time of the coupling reaction. These couplers are disclosed, for example, in U.S. Pat. Nos. 2,875,057, 3,265,506, 3,664,841, 3,408,194, 3,447,928, 3,277,155 and 3,415,652, Japanese Patent Publication No. 13576/1974, Japanese Laid-Open-to-Public Patent Publications Nos. 29,432/1973, 66834/1973, 10736/1974, 122335/1974, 28,834/1975 and 132926/1975. Usable as magenta dye image-forming couplers in the present invention, are those of 5-pyrazolone, pyrazolotriazole, pyrazolinobenzimidazole and indazolone types and 2 equivalent type magenta dye image-forming couplers having split-off groups. These magenta couplers are disclosed, for example, in U.S. Pat. Nos. 2,600,788, 3,062,653, 3,127,269, 3,311,476, 3,419,391, 3,510,429, 3,558,318, 3,684,514 and 3,888,680, Japanese Laid-Open-to-Public Patent Publications Nos. 29639/1974, 111631/1974, 129538/1974 and 13041/1975, Japanese patent applications Nos. 24690/1975, 134470/1975 and 156/1975, British Pat. No. 1,247,493, Belgian Pat. No. 792,525, U.S. Pat. No. 3,061,432, West German Pat. No. 2,156,111, Japanese Patent Publication No. 60479/1971 and Belgian Pat. No. 769,116. Preferably magenta dye image-forming coupler is of 5-pyrazolone type, particularly of 3-anilino-5-pyrazolone type. More preferablly, the anilino in the 3-anilino-5-pyrazolone type is substituted with chlorine at the second position thereof and further with alkyl (or alkenyl) succinimido at the fifth position thereof.

Usable as cyan dye image-forming couplers in the present invention, are those of phenol and naphthol types and 2 equivalent type cyan dye image-forming couplers having split-off groups. These cyan couplers are disclosed, for example, in U.S. Pat. Nos. 2,423,730, 2,474,293, 2,801,171, 2,895,826, 3,476,563, 3,737,326, 3,758,308 and 3,839,044, Japanese Laid-Open-to-Public Patent Publications Nos. 37425/1972, 10135/1975, 25228/1975, 112038/1975, 117422/1975 and 130441/1975.

Typical examples of the dye image-forming couplers used in the present invention are indicated below.

(Y-1)
α-(4-Carboxyphenoxy)-α-pivalyl-2-chloro-5-[γ-2,4-di-t-amylphenoxy)butylamido]acetanilide (Y-2)
α-Benzoyl-2-chloro-5-[γ-(2,4-di-t-amylphenoxy)-butylamido]acetanilide (Y-3)
α-Benzoyl-2-chloro-5-[α-(dodecyloxycarbonyl)-ethoxycarbonyl]acetanilide (Y-4)
α-(4-Carboxyphenoxy)-α-pivalyl-2-chloro-5-[α-(3-pentadecylphenoxy)butylamido]acetanilide (Y-5)
α-(1-Benzyl-2,4-dioxo-3-imidazolidinyl)-α-pivalyl-2-chloro-5-[γ-(2,4-di-t-amylphenoxy)butylamido]-acetanilide (Y-6)
α-[4-(1-Benzyl-2-phenyl-3,5-dioxo-1,2,4-triazolidinyl)]-α-pivalyl-2-chloro-5-[γ-(2,4-di-t-amylphenoxy)butylamido]acetanilide (Y-7)
α-Acetoxy-α-{3-[α-(2,4-di-t-amylphenoxy)-butylamido]-benzoyl}-2-methoxyacetanilide (Y-8)
α{3-[α-(2,4-Di-t-amylphenoxy)butylamido]benzoyl}-2-methoxyacetanilide (Y-9)
α-[4-(4-Benzyloxyphenylsulfonyl)phenoxy]-α-pivalyl-2-chloro-5-[γ(2,4-di-t-amylphenoxy)-butylamido]acetanilide (Y-10)
α-Pivalyl-α-(4,5-dichloro-3(2H)-pyridazo-2-yl)-2-chloro-5-[(hexadecyloxycarbonyl)methoxycarbonyl]-acetanilide (Y-11)
α-Pivalyl-α-[4-(p-chlorophenyl)-5-oxo-$\Delta^2$-tetrazoline-1-yl]-2-chloro-5-[α-(dodecyloxycarbonyl)-ethoxycarbonyl]acetanilide (Y-12)
α-(2,4-Dioxo-5,5-dimethloxazolidine-3-yl)-α-pivalyl-2-chloro-5-[α-(2,4-di-t-amylphenoxy)-butylamido]acetanilide (Y-13)
α-Pivalyl-α-[4-(1-methyl-2-phenyl-3,5-dioxo-1,2,4-triazolidinyl)]-2-chloro-5-[γ-(2,4-di-t-amylphenoxy)-butylamido]acetanilide (Y-14)
α-Pivalyl-α-[4-(p-ethylphenyl)-5-oxo-$\Delta^2$-tetrazoline-1-yl]-2-chloro-5-[γ-(2,4-di-t-amylphenoxy)-butylamido]acetanilide (M-1)
1-(2,4,6-Trichlorophenyl)-3-[3-(2,4-di-t-amyl-phenoxyacetamido)benzamido]-5-pyrazolone (M-2)
  1-(2,4,6-Trichlorophenyl)-3-(3-dodecylsuccimidobenzamido)-5-pyrazolone
(M-3)
  4,4'-methylenebis{1-(2,4,6-trichlorophenyl)-3-[3-(2,4-di-t-amylphenoxyacetamido)benzamido]-5-pyrazolone}
(M-4)
  1-(2,4,6-Trichlorophenyl)-3-(2-chloro-5-octadecylsuccimidoanilino)-5-pyrazolone
(M-5)
  1-(2-Chloro-4,6-dimethylphenyl)-3-{3-[α-(3-pentadecylphenoxy)butylamido]benzamido}-5-pyrazolone
(M-6)
  1-(2,4,6-Trichlorophenyl)-3-(2-chloro-5-octadecylcarbamoylanilino)-5-pyrazolone
(M-7)
  3-Ethoxy-1-{4-[α-(3-pentadecylphenoxy)butylamido]-phenyl}-5-pyrazolone
(M-8)
  1-(2,4,6-Trichlorophenyl)-3-(2-chloro-5-tetradecanamidoanilino)-5-pyrazolone
(M-9)
  1-(2,4,6-Trichlorophenyl)-3-{2-chloro-5-[α-(3-t-butyl-4-hydroxyphenoxy)tetradecanamido]anilino}-5-pyrazolone
(M-10)
  1-(2,4,6-Trichlorophenyl)-3-[3-(2,4-di-t-amylphenoxyacetamido)benzamido]-4-acetoxy-5-pyrazolone
(M-11)
  1-(2,4,6-Trichlorophenyl)-3-[3-(2,4-di-t-amylphenoxyacetamido)benzamido]-4-ethoxycarbonyloxy-5-pyrazolone
(M-12)
  1-(2,4,6-Trichlorophenyl)-3-[3-(2,4-di-t-amylphenoxyacetamido)benzamido]-4-(4-chlorocinnamoyloxy)-5-pyrazolone
(M-13)
  4,4'-Benzylidenebis[1-(2,4,6-trichlorophenyl)-3-{2-chloro-5-[γ-(2,4-di-t-amylphenoxy)butylamido]anilino}-5-pyrazolone]
(M-14)
  4,4'-Benzylidenebis[1-(2,3,4,5,6-pentachlorophenyl)-3-{2-chloro-5-[γ-(2,4-di-t-amylphenoxy)butylamido]anilino}-5-pyrazolone]
(M-15)
  4,4'-(2-Chloro)benzylidenebis[1-(2-chloro-5-dodecylsuccimidoanilino-5-pyrazolone]
(M-16)
  4,4'-Methylenebis[1-(2,4,6-trichlorophenyl)-3-{3-[α-(2,4-di-t-amylphenoxy)butylamido]benzamido}-5-pyrazolone]
(M-17)
  1-(2,6-Dichloro-4-methoxyphenyl)-3-(2-methyl-5-acetamidoanilino)-5-pyrazolone
(M-18)
  1-(2-Chloro-4,6-dimethylphenyl)-3-(2-methyl-5-chloroanilino)-5-pyrazolone
(M-19)
  1-(2,4,6-Trichlorophenyl)-3-(4-nitroanilino)-5-pyrazolone
(M-20)
  1-(2,4,6-Trichlorophenyl)-3-(2-chloro-5-octadecenyl succimido-anilino)-5-pyrazolone
(M-21)
  1-(2,4,6-Trichlorophenyl)-3-(2-chloro-5-tridecanamido anilino)-5-pyrazolone (C-1)
  1-Hydroxy-N-[δ-(2,4-di-t-amylphenoxy)butyl]-2-naphthamide
(C-2)
  2,4-Dichloro-3-methyl-6-(2,4-di-t-amylphenoxyacetamido)phenol
(C-3)
  2,4-Dichloro-3-methyl-6-[α-(2,4-di-t-amylphenoxy)butylamido]phenol
(C-4)
  1-Hydroxy-4-(3-nitrophenylsulfonamido)-N-[δ-(2,4-di-t-amylphenoxy)butyl]-2-naphthamido
(C-5)
  1-Hydroxy-4-[(β-methoxyethyl)carbamoyl]methoxy-N-[δ-(2,4-di-t-amylphenoxy)butyl]-2-naphthamide
(C-6)
  1-Hydroxy-4-(isopropylcarbamoyl)methoxy-N-dodecyl-2-naphthamide
(C-7)
  2-Perfluorobutylamido-5-[α-(2,4-di-t-amylphenoxy)hexanamido]phenol
(C-8)
  1-Hydroxy-4-(4-nitrophenylcarbamoyl)-oxy-N-[δ-(2,4-di-t-amylphenoxy)butyl]-2-naphthamide
(C-9)
  2-(α,α,β,β-Tetrafluoropropionamido)-5-[α-(2,4-di-t-amylphenoxy)butylamido]-phenol
(C-10)
  1-Hydroxy-N-dodecyl-2-naphthamide
(C-11)
  1-Hydroxy-(4-nitro)phenoxy-N-[δ(2,4-di-t-amylphenoxy)butyl]-2-naphthamide
(C-12)
  1-Hydroxy-4-(1-phenyl-5-tetrazolyloxy)-N-[δ-(2,4-di-t-amylphenoxy)butyl]-2-naphthamide
(C-13)
  2-(α,α,β,β-Tetrafluoropropinamido)-4-β-chloroethoxy-5-[α-(2,4-di-t-amylphenoxy)-butylamido]-phenol
(C-14)
  2-Chloro-3-methyl-4-ethylcarbamoylmethoxy-6-[α-(2,4-di-t-amylphenoxy)butylamido]phenol The amount of a coupler used in a silver halide color photosensitive material according to the present invention is generally 5–50 mol%, preferably 10–30 mol%, based on the silver halide, when the coupler is made present in the silver halide color photosensitive material. When the coupler is made present in a developer solution, the amount of coupler used is generally 0.5–3.0 g/l, preferably 1.0–2.0 g/l. In the above cases, yellow, magenta and cyan couplers may be used either singly or in combination of two or more, and the amount of the combination of two or more couplers used is sufficiently within the above-mentioned respective ranges.

Into the silver halide emulsion according to the present invention may also be incorporated, either singly or in combination, hydroquinone derivatives which have been known as antioxidants. These compounds are disclosed, for example, in U.S. Pat. Nos. 3,236,893, 3,062,844, 2,816,028, 2,735,765, 2,732,300, 2,728,659, 2,722,556, 2,710,801, 2,675,314, 2,418,613, 2,403,721, 2,384,658, 2,360,290, and 2,336,327, British Pat. Nos. 557,750 and 557,802, German Laid-Open-to-Public Patent No. 2,149,789, Japanese Patent Publication No. 54116/1969, Japanese Laid-Open-to-Public Patent Publication No. 2128/1971 and Journal of the Organic Chemistry, Vol. 72,772–774. Of the above-mentioned hydroquinone derivatives, those in which the substituent on the organic nucleus is substituted or unsubstituted alkyl are particularly preferable. Particularly preferable as the hydroquinone derivatives, are 2,5-di-octyl-hydroquinone, 2,5-di-tert-amyl-hydroquinone and 2,5-di-tert-butyl-hydroquinone.

The silver halide emulsions used in a silver halide color photosensitive material according to the present invention are those which have generally been prepared by dispersing silver halide grains in a hydrophilic colloid. The silver halides usable in this case include silver chloride, silver bromide, silver iodide, silver chlorobromide, silver iodobromide, silver chloroiodobromide and the mixtures thereof. These silver halides may be prepared according to various methods such as an ammonia process, a neutral process, the so-called conversion process, a simultaneous mixing process and the like. The hydrophilic colloid used in these processes, into which the silver halide is dispersed, generally includes gelatin and gelatin derivatives such as phthalated gelatin and malonized gelatin. The gelatin and gelatin derivatives used may be replaced in whole or in part by albumin, agar, gum arabic, alginic acid, casein, partially hydrolyzed cellulose derivatives, partially hydrolyzed polyvinyl acetate, polyacrylamide, imidized polyacrylamide, polyvinyl pyrrolidone and copolymers of these vinyl compounds. Further, the silver halide emulsions may be optically sensitized using various sensitizing dyes in order to impart light-sensitivity at a desired photosensitive wavelength region to the emulsions. Preferably usable as the sensitizing dyes, are cyanine dyes, merocyanine dyes or composite cyanine dyes disclosed, for example, in U.S. Pat. Nos. 1,939,201, 2,072,908, 2,739,149, 2,294,763, 2,213,995, 2,493,748 and 2,519,001, West German Pat. No. 929,080, and British Pat. No. 505,979, and these dyes may be used either singly or in combination of two or more. Furthermore, the silver halide emulsions used in the present invention may be incorporated, if necessary, with various photographic additives usable either singly or in combination, for example, chemical sensitizers such as thioether compounds, quaternary ammonium salt compounds and polyalkylene oxide compounds: stabilizers such as triazoles, imidazoles, azaindenes, benzothiazoliums, zinc compounds, cadmium compounds and mercaptans: film-hardening agents such as chromium salts, zirconium salts, mucochloric acids, aldehyde type compounds, triazine type compounds, polyepoxy compounds, triethylenephosphoamide type compounds and ethyleneimine type compounds disclosed in Japanese Patent Publications Nos. 7133/1959 and 1872/1971, U.S. Pat. Nos. 682,641, 3,736,320, 3,362,827 and 3,325,287, British Pat. Nos. 686,440 and 1,332,647; plasticizers such as glycerin and dihydroxyalkanes, e.g. 1,5-pentanediol; fluorescent brightening agents; antistatic agents; and coating aids. The silver halide emulsion prepared according to the procedures mentioned previously is incorporated with a dispersion of the present compounds of the aforementioned general formulas, and the resulting emulsion is coated (if necessary, through a sub layer, intermediate layer or protective layer) on a support. The support includes for example, films of cellulose acetate, cellulose nitrate, such as synthetic resins as polycarbonate, polyrthylene terephthalate and polystyrene, a baryta paper, a polyethylene-coated paper, a glass plate and the like. The silver halide emulsion thus coated on the support gives a silver halide color photosensitive material.

The silver halide color photographic material according to the present invention may be applicable as a coupler-containing internal type silver halide color photosensitive material or an external type silver halide photosensitive material wherein a coupler is incorporated into a developer solution, but the present color photographic material is particularly of advantage when used as the coupler-containing internal type silver halide color photosensitive material, which material is exposed to light and then subjected, according to color developing method, to color development. Further, the present color photographic material is applicable as a silver halide color photosensitive material in which a coupler and a color developing agent are made present in the same layer in such a manner that the coupler and the color developing agent are individually protected so that they may not be brought into contact with each other during a period before exposure but, they may be contacted with each other after exposure, or as a coupler-containing silver halide color photosensitive material in which a color developing agent is incorporated into a layer not containing said coupler and, when the layer is processed with an alkali processing solution, the color developing agent is moved to bring into contact with the coupler. In the case where the present color photographic material is used as a silver halide color photosensitive material for use in diffusion transfer, the present compound may be incorporated into a light-sensitive element and/or an image-receiving element of said color photographic material, and the incorporation of the present compound into the image-receiving element is particularly of advantage. When the present color photographic material is applied to reversal process, the material exposed is developed with a black-and-white negative developing solution, followed by white light exposure or treatment in a bath containing such foggant as boron compound, and then subjected to color development using an alkali developer solution containing a color developing agent. In this case, there is no difficulty in incorporating the foggant into the alkali developer solution containing the color developing agent. After the color development, the developed photographic material is subjected to a bleaching treatment using a bleaching solution containing an oxidizing agent such as ferricyanide or a ferric salt of aminopolycarboxylic acids and then subjected to fixing treatment containing such solvent for a silver salt as thiosulfate to remove a silver image and remaining silver halide, whereby a dye image remains. In place of the bleaching and fixing solutions as in the above case, the bleach-fixing treatment can also be carried out by using a one-bath bleach-fixing solution containing an oxidizing agent such as a ferric salt of aminopolycarboxylic acid and a solvent for a silver salt such as thiosulfate. In combination with the color development, bleaching fixing or bleach-fixing, there may be also carried out such treatments as prehardening, neutralizing, water-washing, stopping and stabilizing. The treatment process in which the silver halide color photographic material of the present invention is advantageously developed includes, for example, a process comprising steps of a color development (if necessary followed by water-washing), bleach-fixing, water-washing (if necessary followed by stabilizing step), and drying. The above-mentioned treatment process is carried out at an elevated temperature, for example, 30° C. or above, and in a very short period of time. Typical example of the treatment process and the composition of each of the processing solutions used therein are illustrated below.

| Treatment process (30° C.) | Treatment time |
|---|---|
| Color development | 3 minutes 30 seconds |
| Bleach-fixing | 1 minute 30 seconds |
| Water-washing | 2 minutes |
| Stabilizing | 1 minute |
| Drying | |

Composition of a color developer solution:

| | |
|---|---|
| Benzyl alcohol | 5.0 ml |
| Sodium hexametaphosphate | 2.5 g |
| Anhydrous sodium sulfite | 1.9 g |
| Sodium bromide | 1.4 g |
| Potassium bromide | 0.5 g |
| Borax (Na$_2$B$_4$O$_7$. 10 H$_2$O) | 39.1 g |
| N-ethyl-N-$\beta$-methanesulfonamideethyl-4-aminoaniline sulfate | 5.0 g |
| Water to make | 1 liter |
| Adjusted to pH 10.30 with sodium hydroxide | |

Composition of a bleach-fixing solution:

| | |
|---|---|
| Iron ammonium ethylenediaminetetraacetate | 61.0 g |
| Diammonium ethylenediaminetetraacetate | 5.0 g |
| Ammonium thiosulfate | 124.5 g |
| Sodium metabisulfate | 13.3 g |
| Anhydrous sodium sulfite | 2.7 g |
| Water to make | 1 liter |
| Adjusted to pH 6.5 with ammonia water | |

Composition of a stabilizing solution:

| | |
|---|---|
| Glacial acetic acid | 20 ml |
| 800 ml of water is added thereto, the resulting solution is adjusted to pH with addition of sodium acetate and then | 3.5–4.0 |
| Water to make | 1 liter |

Particularly useful as a color developing agent for use in color development of the silver halide color photosensitive material of the present invention, are primary phenylenediamines, aminophenols and derivatives thereof. For example, salts of such inorganic acids as a hydrochloric acid and a sulfuric acid, or of such organic acids as a p-toluenesulfonic acid, of the following compounds:

N,N-dimethyl-p-phenylenediamine, N,N-diethyl-p-phenylenediamine, N-carbamidomethyl-N-methyl-p-phenylenediamine, N-carbamidomethyl-N-tetrahydrofurfuryl-2-methyl-p-phenylenediamine, N-ethyl-N-carboxymethyl-2-methyl-p-phenylenediamine, N-carbamidomethyl-N-ethyl-2-methyl-p-phenylenediamine, N-ethyl-N-tetrahydrofurfuryl-2-methyl-p-aminophenol, 3-acetylamino-4-aminodimethyl-aniline, N-ethyl-N-$\beta$-methanesulfonamidoethyl-4-amino-aniline, N-ethyl-N-$\beta$-methanesulfonamidoethyl-3-methyl-4-aminoaniline and N-methyl-N-$\beta$-sulfoethyl-p-phenylene-diamine.

The silver halide color photosensitive material comprising the present compounds may be effectively processed by using a color developer solution containing both a primary aromatic amine type color developing agent and an oxidizing agent for use in a redox reaction of a metallic silver image.

When the above-mentioned color developer solution is used, the color developing agent is oxidized with the oxidizing agent and then the oxidized color developing agent couples with a photographic coupler to form a dye image. Such color developer solutions are disclosed, for example, in Japanese Laid-Open-to-Public Patent Publication No. 9729/1973, and the oxidizing agent suitable for this purpose is cobalt complex salts having a coordination number of 6. The treatment of color photosensitive materials involving the use of such color developer solution is particularly effective in processing the so-called silver-saved color photographic material having a silver content smaller than that of ordinary silver halide color photographic materials.

Particularly useful as the cobalt complex salts in the above-mentioned color developer solution, are those which contain ligands selected from the group consisting of ethylenediamine, diethylenetriamine, triethylenetetramine, amine, nitrate, nitrite, azide, chloride, thiocyanate, isothiocyanate, water and carbonate, and which contain (1) at least two ethylenediamine ligands, or (2) at least five amine ligands, or (3) at least one triethylenetriamine ligand. Particularly preferable cobalt complex salts are, for example, those which are represented by the following formulas.

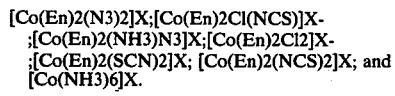

[Co(En)2(N3)2]X;[Co(En)2Cl(NCS)]X-;[Co(En)2(NH3)N3]X;[Co(En)2Cl2]X-;[Co(En)2(SCN)2]X; [Co(En)2(NCS)2]X; and [Co(NH3)6]X.

In the above formulas, En represents ethylenediamine, and X represents at least one anion selected from the group consisting of chloride, bromide, nitrite, nitrate, perchlorate, acetate, carbonate, sulfite, sulfate, hydrochloride, thiocyanate, isothiocyanate and hydroxide. The most preferable complex salts are hexamine salts of cobalt, for example, chloride, bromide, sulfite, sulfate, perchlorate, nitrite and acetate. The amount of a cobalt complex salt used in the color developer solution is generally in the concentration range of from about 0.1 to about 50 g per liter of the color developer solution, more preferably in a range of from about 1 to about 15 g.

Further, the silver halide color photographic material comprising the present compounds is also applicable to a color photographic treatment process wherein the material is developed after exposure in a color developing solution containing a primery aromatic amine type color developing agent and then brought into contact with an amplifying solution in an amplifying bath, which amplifying solution contains the aforementioned oxidizing agent, e.g. a cobalt complex salt having coordination number of 6, preferably in the presence of a color developing agent which may be received during color development step into a light-sensitive layer and also may be moved to the amplifying bath. For the above purpose, other oxidizing agents; for example, an aqueous hydrogen peroxide solution disclosed in Japanese Pat. application No. 80321/1974, may also preferably be usable. The above-mentioned amplifying solution, when used in the treatment of a silver halide color photographic material, preferably contains a silver halide-development inhibitor in addition to the oxidizing agent. In such case, the amplifying step can be carried out in a chamber under illumination. According to this method, the state of formation of dyes can visually be observed and hence the amplifying step can be stopped as soon as a desired dye density is attained. Preferable as the development inhibitors used in this method, are water-soluble bromide compounds such as potassium bromide and such heterocyclic compounds containing neither a mercapto group nor an ionic iodide group as tetrazoles, azaindenes and triazoles.

The concentration of a cobalt complex salt present in the amplifying solution is generally about 0.2 to about 20 g/l, most preferably, about 1 to about 15 g/l, and that of the aqueous hydrogen peroxide solution is generally about 0.01 to 10%, most preferably 0.5 to 5%. In the case where a water-soluble bromide is used as a development inhibitor, this substance is used in an amount of about 1 to about 40 g/l in the amplifying solution. On the other hand, the development inhibitor comprising a compound of heterocyclic structure is used usually in a concentration of about 0.01 to about 3 g/l. The amplifying bath used is generally adjusted to pH 6-14, preferably pH 8-12.

In addition to the aforesaid development inhibitor, the amplifying solution may contain, if necessary, development promoters, stabilizers, water-softening agents, thickening agents, agents for prevention on an uneven treatment and the like.

Further, the present compounds exhibit sufficiently their effect on prevention of fading of light-sensitive materials of diazo type.

The present invention is illustrated in concrete below with reference to examples, but embodiments of the invention are not limited to these examples.

spective solvents. Each of the solutions thus prepared was incorporated with 120 mg of 2,5-di-t-octylhydroquinone and then incorporated into 500 cc of a 5% aqueous gelatin solution containing 2.5 g of sodium dodecylbenzene sulfonate. The resulting solution was subjected to a homogenizer to obtain a dispersion. The dispersion thus obtained was incorporated into 100 cc of a green-sensitive silver chlorobromide emulsion (containing 40 mol% of silver chloride), and the emulsion was charged with 10 ml of a 2% methanol solution of N,N',N''-triacroyl-6H-S-triazine. The resulting emulsion was coated on a polyethylene-coated paper and then dried to obtain a light-sensitive silver halide photographic material (sample Nos. 1-12). Each of the samples thus prepared was exposed to light through an optical wedge and then processed according to the treatment process as indicated in the main text, followed by exposure for 50, 100, 200, 300 and 500 hours, respectively, by means of a Xenon fade-o-meter. Thereafter, each sample thus exposed was subjected to Sakura Color densitometer PD-6 (manufactured by Konishiroku Photo Industry Co., Ltd.) to measure a percentage ($D/D_o \times 100$) of density (D) after exposure against density ($D_o = 1.0$) before exposure, and a dye fading ratio was measured under a green light and a Y-stain increasing ratio of an unexposed area was measured under a blue light. The results obtained were as shown in Table 1-2.

Table 1 - 1

| No. | Coupler and its amount added | | Exemplified compound and its amount added | | High boiling solvent and its amount added | | Low boiling solvent and its amount added | |
|---|---|---|---|---|---|---|---|---|
| 1 | (M-1) | 36 g | — | — | DBP | 36 cc | EA | 100 cc |
| 2 | " | " | (2) | 11 g | " | " | " | " |
| 3 | " | " | (5) | " | " | " | " | " |
| 4 | " | " | (31) | " | " | " | " | " |
| 5 | (M-3) | 39 g | — | — | TPP | 39 cc | MA | 100 cc |
| 6 | " | " | (6) | 12 g | " | " | " | " |
| 7 | " | " | (27) | " | " | " | " | " |
| 8 | " | " | (31) | " | " | " | " | " |
| 9 | (M-4) | 39 g | — | — | DBP | 19 cc | EA | 100 cc |
|   |       |      |     |     | TCP | 19 cc |    |        |
| 10 | " | " | (12) | 12 g | " | " | " | " |
| 11 | " | " | (2) | 8 g | " | " | " | " |
|   |   |   | (31) | 4 g |   |   |   |   |
| 12 | " | " | (37) | 12 g | " | " | " | " |

Notes:
DBP: Dibutyl phthalate
TCP: Tricresyl phosphate
TPP: Triphenyl phosphate
EA: Ethyl acetate
MA: Methyl acetate
The same shall apply hereinafter.

EXAMPLE 1

As indicated in Table 1—1, magenta couplers and the present compounds were individually dissolved in re- Table 1 - 2

| Irradiation time (hr) Sample | Dye fading ratio | | | | | Y-stain increasing ratio | | | | |
|---|---|---|---|---|---|---|---|---|---|---|
|  | 50 | 100 | 200 | 300 | 500 | 50 | 100 | 200 | 300 | 500 |
| 1 | 73 | 51 | 32 | 10 | 0 | 430 | 926 | 2,500 | 3,000 | 2,400 |
| 2 | 92 | 85 | 65 | 56 | 35 | 275 | 775 | 1,820 | 2,100 | 1,650 |
| 3 | 94 | 87 | 70 | 52 | 30 | 293 | 791 | 1,880 | 2,300 | 1,780 |
| 4 | 95 | 89 | 72 | 60 | 40 | 292 | 711 | 1,721 | 1,920 | 1,500 |
| 5 | 71 | 53 | 35 | 20 | 2 | 450 | 930 | 2,600 | 2,900 | 2,300 |
| 6 | 95 | 89 | 75 | 63 | 47 | 315 | 650 | 1,600 | 1,800 | 1,500 |
| 7 | 99 | 93 | 82 | 62 | 38 | 290 | 560 | 1,450 | 1,950 | 1,650 |
| 8 | 98 | 92 | 80 | 71 | 55 | 300 | 605 | 1,550 | 1,700 | 1,400 |
| 9 | 90 | 73 | 42 | 24 | 5 | 520 | 1,200 | 3,200 | 3,300 | 2,500 |
| 10 | 100 | 96 | 90 | 71 | 42 | 326 | 810 | 2,200 | 2,500 | 2,100 |
| 11 | 100 | 95 | 89 | 73 | 49 | 295 | 795 | 1,930 | 2,200 | 1,850 |

Table 1 - 2-continued

| Irradiation time (hr) | | Dye fading ratio | | | | | Y-stain increasing ratio | | | | |
|---|---|---|---|---|---|---|---|---|---|---|---|
| Sample | | 50 | 100 | 200 | 300 | 500 | 50 | 100 | 200 | 300 | 500 |
| 12 | | 100 | 93 | 85 | 73 | 53 | 280 | 775 | 1,826 | 2,100 | 1,760 |
| Comparison | −1 | 82 | 60 | 43 | 31 | 17 | 397 | 906 | 2,200 | 2,400 | 2,100 |
| " | −2 | 87 | 72 | 54 | 49 | 28 | 395 | 875 | 2,200 | 2,500 | 2,200 |
| " | −3 | 89 | 75 | 55 | 48 | 27 | 413 | 865 | 2,120 | 2,450 | 2,150 |
| " | −4 | 82 | 74 | 50 | 35 | 20 | 410 | 860 | 2,400 | 2,700 | 2,300 |
| " | −5 | 89 | 80 | 63 | 52 | 36 | 370 | 830 | 2,200 | 2,550 | 2,150 |
| " | −6 | 90 | 82 | 61 | 50 | 33 | 365 | 820 | 2,240 | 2,600 | 2,160 |
| " | −7 | 90 | 76 | 58 | 44 | 20 | 408 | 1,080 | 3,100 | 3,200 | 2,400 |
| " | −8 | 93 | 82 | 72 | 57 | 35 | 425 | 925 | 2,800 | 3,000 | 2,700 |
| " | −9 | 91 | 83 | 75 | 55 | 32 | 435 | 975 | 2,650 | 2,900 | 2,650 |

The comparative samples shown in Table 1-2 were prepared in the same manner as in this example but using couplers and fading-preventive agents in combination as shown in Table 1-3.

Table 1 - 3

| Comparative sample No. | Coupler and an ammount added (g) | | Known fade-preventive agent and its amount added (g) | |
|---|---|---|---|---|
| 1 | (M-1) | 36 | (I) | 11 |
| 2 | " | " | (II) | 11 |
| 3 | " | " | (III) | 11 |
| 4 | (M-3) | 36 | (I) | 12 |
| 5 | " | " | (II) | 12 |
| 6 | " | " | (III) | 12 |
| 7 | (M-4) | 39 | (I) | 12 |
| 8 | " | " | (II) | 12 |
| 9 | " | " | (III) | 12 |

The known fading-preventive agents used in the comparative samples were such compounds as having the following structures, respectively.

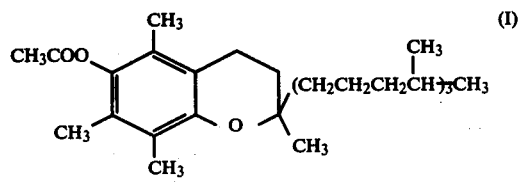

(I)

(Disclosed in U.S. Patent 4,015,990)

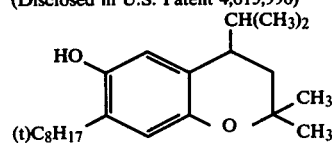

(II)

(Disclosed in U.S. Patent 3,432,300)

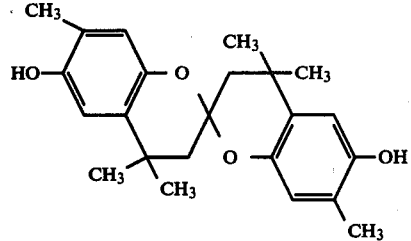

(III)

(Disclosed in Japanese Patent Publication No. 20977/1974)

From the results shown in Table 1-2, it is understood that the present compounds are apparently excellent in a fading-preventive effect on the magenta dye images and the effect of the present compounds is superior to that of the fading-preventive agents hitherto known, and further that the present compounds effectively prevent a Y-stain of an unexposed area and their effect thereon excellently lasts for a long period of time.

EXAMPLE 2

As shown in Table 2-1, yellow couplers and the present compounds were individually dissolved in respective solvents to prepare solutions. Each of the solutions thus prepared was incorporated with 150 mg of 2,5-di-t-octylhydroquinone and then incorporated into 500 cc of a 5% aqueous gelatin solution containing 3.0 g of sodium dodecylbenzenesulfonate. The resulting solution was subjected to a homogenizer to obtain a dispersion. The dispersion thus obtained was incorporated into 1000 cc of a blue-sensitive silver chlorobromide emulsion (containing 10 mol% of silver chloride), and the emulsion was charged with 10 ml of a 5% methanol solution of triethylenesulfonamide as a film hardener. The resulting emulsion was coated on a polyethylene-coated paper and then dried to obtain a light-sensitive silver halide photographic material (sample Nos. 1-8). Each of the samples thus obtained was treated in the same manner as in Example 1 and then exposed for 50 and 100 hours by means of a Xenon Fade-o-Meter. Thereafter, each sample thus irradiated was subjected to measurement in the same manner as in Example 1 except that a dye density was measured under a blue light. The results obtained were as shown in Table 2—2.

Table 2 - 1

| No. | Coupler and its amount added (g) | | Examplified Compound and its amount added (g) | | High boiling solvent and its amount added (cc) | | Low boiling solvent and its amount added (cc) | |
|---|---|---|---|---|---|---|---|---|
| 1 | (Y-3) | 61 | — | — | DBP | 61 | EA | 120 |
| 2 | " | " | (2) | 18 | " | " | " | " |
| 3 | " | " | (12) | " | " | " | " | " |
| 4 | " | " | (35) | " | " | " | " | " |
| 5 | (Y-5) | 76 | — | — | " | " | " | " |
| 6 | " | " | (4) | 23 | TCP | 76 | " | " |
| 7 | " | " | (7) | " | " | " | " | " |
| 8 | " | " | (31) | " | " | " | " | " |

Table 2 - 2

| Sample No. | | Dye fading ratio | | Y-stain increasing ratio | |
|---|---|---|---|---|---|
| | | 50 hrs | 100 hrs | 50 hrs | 100 hrs |
| 1 | | 58 | 15 | 138 | 150 |
| 2 | | 68 | 26 | 110 | 125 |
| 3 | | 70 | 20 | 120 | 132 |
| 4 | | 72 | 32 | 110 | 120 |
| 5 | | 90 | 80 | 126 | 145 |
| 6 | | 94 | 87 | 115 | 127 |
| 7 | | 95 | 85 | 119 | 132 |
| 8 | | 93 | 90 | 112 | 123 |
| Comparison | −1 | 59 | 14 | 129 | 150 |
| | −2 | 29 | 6 | 140 | 162 |
| | −3 | 32 | 7 | 135 | 155 |
| | −4 | 91 | 80 | 123 | 145 |
| | −5 | 75 | 64 | 130 | 157 |
| | −6 | 63 | 57 | 126 | 152 |

The comparative samples shown in Table 2—2 were prepared in the same manner as in this example, except that the couplers were used in combination with the fading-preventing agents in the manner as shown in table 2–3.

Table 2 - 3

| Comparative Sample No. | Coupler and its amount added (g) | | Known fading- and its amount added (g) | |
|---|---|---|---|---|
| 1 | (Y-3) | 61 | I | 18 |
| 2 | " | " | II | " |
| 3 | " | " | III | " |
| 4 | (Y-5) | 76 | I | 23 |
| 5 | " | " | II | " |
| 6 | " | " | III | " |

From the results shown in Table 2—2, it is understood that the known compounds do not exhibit any effect on prevention of fading of yellow dye images, but rather have an effect to promoting the fading, whereas the present compounds have an excellent effect on prevention of fading of yellow dye images and are capable of effectively preventing an unexposed area from Y-stain.

EXAMPLE 3

A mixture of 46 g of cyan coupler (C-1), 200 mg of 2,5-di-t-octylhydroquinone and a fading-preventive agent (each shown in Table 3) was dissolved in a mixture of 40 g dibutylphthalate and 120 g of ethyl acetate to prepare a solution. This solution was incorporated into 500 cc of a 5% aqueous gelatin solution containing sodium dodecylbenzenesulfonate and then subjected to a homogenizer to prepare a dispersion. The dispersion thus obtained was incorporated into 1000 cc of a red-sensitive silver chlorobromide emulsion (containing 20 mol% of silver chloride), and the emulsion was charged with 20 ml of a 4% aqueous solution of 2,4-dichloro-6-hydroxy-S-triazine sodium as a film hardener. The resulting emulsion was coated on a polyethylene-coated paper to obtain a light-sensitive silver halide photographic material. Separately, the same procedure as above was repeated, except that 45 g of cyan coupler (C-3) was used in place of cyan coupler (C-1), to obtain a light-sensitive silver halide photographic material. Each of the samples thus prepared was treated in the same manner as in Example 1 and then irradiated for 150 and 300 hours with a Xenon Fade-O-meter. Thereafter, each sample was subjected to measurement in the same manner as in Example 1, except that a dye sensity was measured under a red light. The results obtained were as shown in Table 3.

As is clear from the results shown in Table 3, it is understood that the present compounds exhibit favorable effect on prevention of fading or cyan dye images, as compared with the known fading-preventive agents.

Table 3

| | | | Dye fading ratio Cyan coupler | | | |
|---|---|---|---|---|---|---|
| | | | C-1 | | C-2 | |
| NO. | Fading-preventive agent and its amount (g) | | 150 hrs | 300 hrs | 150 hrs | 300 hrs |
| 1 | — | | 86 | 74 | 91 | 82 |
| 2 | Compound (7) | 12 | 92 | 79 | 93 | 85 |
| 3 | Compound (30) | 12 | 93 | 83 | 93 | 87 |
| 4 | Known fading preventive agent (I) | 12 | 87 | 74 | 89 | 80 |
| 5 | " (II) | 12 | 89 | 75 | 89 | 80 |
| 6 | " (III) | 12 | 89 | 75 | 89 | 80 |
| 7 | Compound (2) | 12 | 93 | 80 | 93 | 86 |
| 8 | Compound (48) | 12 | 93 | 81 | 93 | 86 |

EXAMPLE 4

On the surface of a polyethylene-coated paper support were coated successively the following layers and then dried to prepare a light-sensitive silver halide color photographic material. (Sample 1)

First layer:

The first layer coated on the support was a blue-sensitive silver halide emulsion layer comprising a silver chlorobromide emulsion containing 10 mol% of silver chloride, said emulsion containing 400 g of gelatin per mole of the silver halide, being sensitized with $2.5 \times 10^{-4}$ mole, based on mole of the silver halide, of a sensitizing dye having the following structure, containing $2 \times 10^{-1}$ mole, based on mole of the silver halide, of yellow coupler (Y-6) dissolved in dibutyl phthalate and dispersed in said emulsion, and being coated on the support so that the amount of silver became 400 mg/cm$^2$:

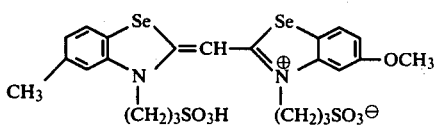

Second layer:
The second layer is a gelatin layer coated on the first layer so that a dry thickness of the gelatin layer became 1 micron.

Third layer:
The third layer was a green-sensitive silver halide emulsion layer comprising a silver chlorobromide emulsion containing 40 mol% of silver chloride, said emulsion containing 500 g of gelatin per mole of the silver halide, being sensitized with $2.5 \times 10^{-4}$ mole, based on mole of the silver halide, of a sensitizing dye having the following structure, containing $2 \times 10^{-1}$ mole, based on mole of the silver halide, of magenta coupler (M-14) disolved in tricresyl phosphate and dispersed in the emulsion, and being coated on the second layer so that the amount of silver became 500 mg/m$^2$:

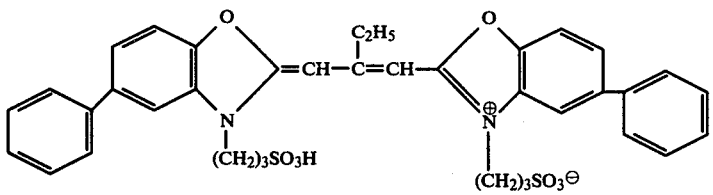

Fourth layer:
The fourth layer was a gelatin layer of 1 micron in thickness containing di-t-octylhydroquinone dissolved in dibutyl phthalate and dispersed in the gelatin solution in an amount of 30 mg/m$^2$.

Fifth layer:
The fifth layer was a red-sensitive silver halide emulsion layer comprising a silver chlorobromide emulsion containing 20 mol% of silver chloride, said emulsion containing 500 g of gelatin per mole of the silver halide, being sensitized with $2.5 \times 10^{-4}$ mole, based on mole of the silver halide, of a sensitizing dye having the following structure, containing $2 \times 10^{-1}$ mole, based on mole of the silver halide, of cyan coupler (C-3) dissolved in tricresyl phosphate and dispersed in the emulsion, and being coated on the fourth layer so that the amount of sliver became 500 mg/m$^2$:

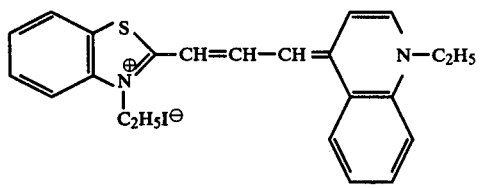

Sixth layer:
The sixth layer was a protective layer (gelatin layer) coated on the fifth layer so that a dry thickness of the layer became 1 micron.

The silver halide emulsions used respectively in the light-sensitive layers (the first, second and third layers) were individually prepared according to the procedure disclosed in Japanese Pat. Publication No. 772/1971. Each emulsion was chemically sensitized with sodium thiosulfate pentahydrate and incorporated with 4-hydroxy-6-methyl-1,3,3$_a$,7-tetrazaindene as a stabilizer, bis(vinylsulfonylmethyl)ether as a film hardener and saponin as a coating aid.

Subsequently, sample 2 was prepared by repeating the same procedure as in the case of the sample 1, except that each of the first, third and fifth layers was incorporated with a dispersion of the present compound (30) in an amount of 30 wt% based on each of the couplers present in said layer.

Further, samples 3 and 4 were prepared by using known compounds (II) and (III), respectively, in the sample 2 in place of the present compounds.

Each of the samples thus prepared was exposed through an optical wedge to a blue light, a green light, and a red light. The exposed sample was treated in accordance with the procedure described in Example 1 and then irradiated for 100 hours by means of a Xenon Fade-o-meter. The sample thus irradiated was measured in dye density to obtain the results shown in Table 4.

Table 4

| Sample No. | Dye fading ratio | | | Y-stain increasing ratio |
|---|---|---|---|---|
| | Yellow | Magenta | Cyan | |
| 1 | 90 | 75 | 93 | 450 |
| 2 | 93 | 96 | 95 | 145 |
| 3 | 60 | 82 | 92 | 280 |
| 4 | 64 | 83 | 92 | 290 |

As is clear from the results shown in Table 4, it is understood that the known fading-preventive agents have no preventive effect on fading of dye images other than magenta dye images, or rather have a tendency to promote the fading, whereas the present compounds are quite excellent fading-preventive agents which have not only excellent effect even in preventing magenta dye images from fading but also in preventing yellow and cyan dye images from fading.

EXAMPLE 5

A solution of 12 g of compound (31) in 11 g of dibutyl phthalate was incorporated into 120 cc of a 5% aqueous gelatin solution containing sodium dodecylbenzene sulfonate, and the resulting mixture was subjected to a homogenizer to prepare a dispersion. The dispersion thus prepared was incorporated into 300 cc of a green-sensitive silver chlorobromide emulsion (containing 40 mol% of silver chloride), and the emulsion was coated on a polyethylene-coated paper and then dried to obtain a light-sensitive silver halide photographic material.

This light-sensitive silver halide photographic material was exposed to light through an optical wedge according to a sensitometry method, and then processed at a temperature of 24° C. according to the following steps in succession.

| Treatment steps: | |
|---|---|
| First development | 5 minutes |
| Water-washing | 4 minutes |
| Exposure to light | |
| Color development | 3 minutes |

-continued

Treatment steps:

| | |
|---|---|
| Water-washing | 4 minutes |
| Bleaching | 4 minutes |
| Fixing | 4 minutes |
| Water-washing | 10 minutes |

The first developer solution, color developer solution, bleaching and fixing solutions used in the above treatment steps individually had the following composition.

Composition of a first developer solution:

| | | |
|---|---|---|
| Anhydrous sodium bisulfite | 8.0 | g |
| Phenidone | 0.35 | g |
| Anhydrous sodium sulfite | 37.0 | g |
| Hydroquinone | 5.5 | g |
| Anhydrous sodium carbonate | 28.2 | g |
| Sodium thiocyanate | 1.38 | g |
| Anhydrous sodium bromide | 1.30 | g |
| Potassium iodide (0.1% aqueous solution) | 13.0 | ml |
| water to make | 1 | liter |
| Adjusted to pH 9.9 | | |

Composition of a color developer solution:

| | | |
|---|---|---|
| Anhydrous sodium sulfite | 10.0 | g |
| N,N-diethyl-p-phenylenediamine hydrochloride | 3.0 | g |
| Magenta coupler (M-19) | 1.5 | g |
| Water to make | 1 | liter |
| Adjusted to pH 11.5 with sodium hydroxide | | |

Composition of a bleaching solution.

| | | |
|---|---|---|
| Anhydrous sodium bromide | 43.0 | g |
| Potassium ferricyanide | 165.0 | g |
| Borax ($Na_2B_4O_7 \cdot 10 H_2O$) | 1.2 | g |
| Water to make | 1 | liter |

Composition of a fixing solution:

| | | |
|---|---|---|
| Sodium thiosulfate (pentahydrate) | 200 | g |
| Anhydrous sodium sulfate | 100 | g |
| Anhydrous disodium phosphate | 15.0 | g |
| Water to make | 1 | liter |

The thus obtained color photographic material was irradiated for 100 hours by means of a Xenon Fade-o-meter. Thereafter, dye fading ratio and Y-stain increasing ratio were obtained in the same manner as in Example 1. For comparison, there were used in this example a color photographic material prepared according to this example but using the known compound (III) in place of the present compound, and as a blank a color photographic material prepared according to this example but without incorporating compound (31) thereinto. The results obtained were as shown in Table 5.

Table 5

| Sample No. | Fading-preventive agent | Dye fading ratio | Y-stain increasing ratio |
|---|---|---|---|
| 1 | Blank | 65 | 480 |
| 2 | Compound (31) | 94 | 118 |
| 3 | Known compound (III) | 87 | 165 |

From the results shown in Table 5, it is understood that even in the case of a light-sensitive silver halide photographic material containing no coupler, the present compound prevent Y-stain and has an excellent fading-preventive effect.

EXAMPLE 6

A magenta coupler and the present compound or a know fading-preventive agent as set forth in Table 6 - 1 were dissolved in such solvent as shown in the table. 120 mg of 2,5-di-t-octylhydroquinone was further added into the resulting to obtain a solution. The solution was then added into 500 cc of a 5% aqueous gelatin solution containing 2.5 g of sodium dodecylbenzenesulfonate and the resulting was well dispersed by a homogenizer. The thus obtained dispersion was added into 1000 cc of a green sensitive silver chloro-bromide emulsion (containing 40 mol% of silver chloride). 10 ml of a 2% methanol solution of N-ethyl-N'-γ-trimethylammonium propylcarbodiimide-p-toluenesulfonate was addditionally incorporated thereinto. The resulting was coated on a polyethylene-coated paper and dried to obtain a silver halide photosensitive element. The same procedure was repeated to obtain samples 1 to 18 and comparative samples 1 to 3. These samples were individually subjected to a wedge exposure and then successively processed as follows:

| | | processing temperature | processing time |
|---|---|---|---|
| 1 | Color development | 32.2° C. | 1 minute 30 seconds |
| 2 | bleach-fixing | 32.2° C. | 1 minute 20 seconds |
| 3 | washing | 32.2° C. | 30 seconds |

Composition of the developer

| | | |
|---|---|---|
| Water | 800 | cc |
| Sodium hexameta phosphate | 6.5 | g |
| Anhydrous sodium sulfite | 20 | g |
| 4-Amino-3-methyl-N,N-diethyl aniline hydrochloride | 3.2 | g |
| Sodium carbonate | 20 | g |
| Sodium bromide | 1.8 | g |
| Additional water to make | 1 | liter |

Composition of the bleach-fixing solution
The composition was as set forth before.

The thus processed samples were exposed to sun light through transparent window glass for one, two, and three months to test fading-preventability against sun light. The results obtained are shown in Table 6 - 2. A method of the measurement was as same as that in Example 1.

Table 6 - 1

| Sample No. | Coupler and its amount added | | Exemplified compound and its amount added | High boiling solvent and its amount used (cc) | | Low boiling solvent and its amount used | |
|---|---|---|---|---|---|---|---|
| 1 | (M-4) | 398 | — | DBP | 39 | EA | 100 cc |
| 2 | " | " | (40) 8.1 g | " | " | " | " |
| 3 | " | " | (41) 8.1 g | " | " | " | " |

Table 6 - 1-continued

| Sample No. | Coupler and its amount added | Exemplified compound and its amount added | High boiling solvent and its amount used (cc) | Low boiling solvent and its amount used |
|---|---|---|---|---|
| 4 | " " | (42) 8.6 g | " " | " " |
| 5 | " " | (43) 9.0 g | " " | " " |
| 6 | " " | (2) 9.9 g | " " | " " |
| 7 | " " | (44) 9.9 g | " " | " " |
| 8 | " " | (45) 9.9 g | " " | " " |
| 9 | " " | (46) 10.3 g | " " | " " |
| 10 | " " | (47) 12.7 g | " { DBP 16 / TCP 20 } | " " |
| 11 | " " | (48) 13.3 g | " { DBP 10 / TCP 10 } | " " |
| 12 | " " | (49) 7.1 g | " DBP 36 | " " |
| 13 | " " | (49) 14.2 g | " " | " " |
| 14 | " " | (49) 20 g | " " | " " |
| 15 | " " | (49) 39 g | " " | " " |
| 16 | " " | (31) 18.2 g | " 39 | " " |
| 17 | " " | (35) 15.3 g | " " | " " |
| 18 | " " | (68) 13.2 g | " " | " " |
| Comparison −1 | " " | known fading-preventive agent I 14.6 g | " " | " " |
| −2 | " " | " II 10.3 | " " | " " |
| −3 | " " | " III 11.4 g | " " | " " |

Table 6 - 2

| Irradiation Time (month) Sample No. | Dye fading ratio | | | Y-stain increasing ratio | | |
|---|---|---|---|---|---|---|
| | 1 | 2 | 3 | 1 | 2 | 3 |
| 1 | 45 | 25 | 10 | 3,100 | 3,300 | 2,950 |
| 2 | 76 | 67 | 61 | 2,300 | 2,500 | 2,200 |
| 3 | 77 | 68 | 61 | 2,350 | 2,500 | 2,200 |
| 4 | 77 | 67 | 62 | 2,250 | 2,430 | 2,150 |
| 5 | 76 | 68 | 62 | 2,200 | 2,300 | 2,020 |
| 6 | 82 | 72 | 66 | 1,900 | 2,100 | 1,800 |
| 7 | 81 | 71 | 65 | 1,950 | 2,200 | 1,800 |
| 8 | 81 | 73 | 64 | 2,000 | 2,150 | 1,900 |
| 9 | 85 | 72 | 66 | 1,980 | 2,050 | 1,800 |
| 10 | 95 | 80 | 75 | 1,800 | 2,000 | 1,700 |
| 11 | 95 | 84 | 77 | 1,760 | 1,900 | 1,650 |
| 12 | 90 | 80 | 74 | 1,750 | 1,900 | 1,650 |
| 13 | 96 | 85 | 78 | 1,730 | 1,850 | 1,600 |
| 14 | 97 | 87 | 80 | 1,700 | 1,830 | 1,600 |
| 15 | 98 | 90 | 80 | 1,700 | 1,830 | 1,600 |
| 16 | 98 | 92 | 82 | 1,690 | 1,790 | 1,500 |
| 17 | 97 | 90 | 81 | 1,700 | 1,820 | 1,550 |
| 18 | 90 | 82 | 77 | 1,750 | 1,850 | 1,600 |
| Comparison −1 | 60 | 35 | 20 | 2,800 | 2,950 | 2,750 |
| " −2 | 74 | 64 | 59 | 2,500 | 2,700 | 2,460 |
| " −3 | 75 | 68 | 48 | 2,400 | 2,540 | 2,340 |

As clear from Table 6-2, the present compunds are excellent in fading-prevention as to magenta images and the degree thereof is superior to that by the known fading-preventive agent. Furthermore, the present compounds prevent unexposed areas from yellow staining and such the excellent effect lasts for a long period of time. Moreover, it will be understood that the higher alkoxy at the 6-position of chromane gives the better results when compared with a lower alkoxy. Such alkoxy as containing not less than 8 carbon atoms, especially more than 12 carbon atoms inclusive, gives much better results.

EXAMPLE 7

Samples 1 and 2 were prepared according to the exactly same procedure as for sample 1 of Example 4, except that magenta coupler (M-20) was employed in an amount of $1.5 \times 10^{-1}$ mole per mole of silver halide in place of magenta coupler (M-14) to obtain sample 1 and that magenta coupler (M-21) was employed in an amount of $1.5 \times 10^{-1}$ mole per mole of silver halide in place of magenta coupler (M-14) to obtain sample 2.

On the other hand, each of present compounds (40), (48) and (57) were added into the emulsion along with the coupler in an amount of 30 wt.% based on the coupler after dispersed, with respect to each of the first, third and fifth photosensitive layers of sample 1 to obtain samples 3, 4 and 5.

As same as the above, present compounds (40), (48) and (57) were employed to obtain samples 6, 7 and 8. Moreover, the known fading-preventive agent was employed in place of the present compound in sample 3 in a same amount of the present compound. This procedure was repeated as to known fading preventive agents (I), (II) and (III) to obtain samples 9, 10 and 11 respectively.

In sample 5, the same procedure as above was repeated as to known fading-preventive agents (I), (II) and (III) to obtain samples 12, 13 and 14. The thus obtained samples were individually subjected to an wedge exposure by each of a blue light, a green light and a red light, and then processed according to the method set forth in Example 1. The so-processed samples were exposed to sun light through transparent window glass to test fading-preventivity against a sun light exposure. The results obtained are as follows:

Table 7

| Sample No. | Dye fading ratio Y | Dye fading ratio M | Dye fading ratio C | Y-stain increasing ratio |
|---|---|---|---|---|
| 1 | 42 | 15 | 80 | 350 |
| 2 | 42 | 13 | 80 | 355 |
| 3 | 46 | 55 | 88 | 200 |
| 4 | 55 | 85 | 93 | 120 |
| 5 | 52 | 75 | 91 | 130 |
| 6 | 46 | 50 | 88 | 210 |
| 7 | 55 | 80 | 93 | 125 |
| 8 | 52 | 70 | 91 | 140 |
| 9 | 42 | 25 | 77 | 300 |
| 10 | 30 | 50 | 70 | 260 |
| 11 | 33 | 45 | 70 | 280 |
| 12 | 42 | 15 | 77 | 315 |
| 13 | 30 | 50 | 70 | 270 |
| 14 | 33 | 40 | 70 | 290 |

As obviously seen from Table 7, the present compounds are excellent in fading-preventing effects on magenta dye images. The effects are superior to those by the known fading-preventive agents.

In addition, the known agents do not show fading-prevention effects on other than magenta dye images and do show even a tendency of accelation in fading. On the other hand, the present compounds have the above-mentioned excellent effects on yellow and cyan dye images as well as magenta dye images.

Moreover, it will be understood that the higher alkoxy at the 6-position of chromane gives the better results when compared with lower alkoxy.

What is claimed is:

1. A color photosensitive material comprising a support and a silver halide photosensitive layer said material containing a compound represented by the following formulas:

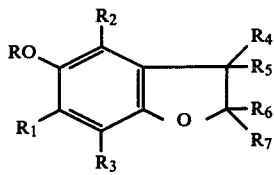

Formula (II)

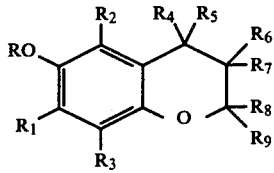

Formula (III)

or

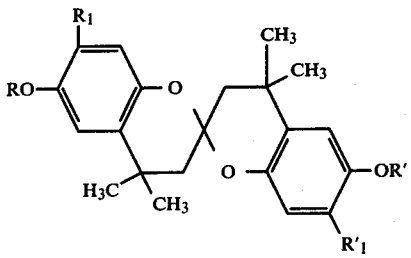

Formula (IV)

wherein R represents an alkyl group, an alkenyl group, a cycloalkyl group, an aryl group, or a heterocyclic group selected from piperadine, morpholine, imidazoline, thiazoline, pyridine, pyrimidine, and triazine; $R_1$, $R_2$ and $R_3$ individually represent hydrogen, halogen, an alkyl group, an akylthio group, an alkoxy group, and aryl group, an aryloxy group, an arylthio group, an acyl group, an acylamino group, a diacylamino group, an acyloxy group, a sulfonamido group, an alkylamino group, a cycloalkyl group or an alkoxycarbonyl group; R' is as defined for R; $R'_1$ is as defined for $R_1$; $R_4$, $R_5$, $R_6$, $R_7$, $R_8$ and $R_9$ individually represent hydrogen, an alkyl group, an alkoxy group, an alkylthio group, an alkenyl group, an alkenyloxy group, an aryl group, an aryloxy group, an N-substituted amino group or a heterocyclic group selected from piperadine, morpholine, imadolizine, thiazoline, pyridine, pyrimidine, triazine, provided that $R_8$ and $R_9$ can cooperatively cyclized to form a cyclohexane ring, which may be substituted with alkyl.

2. A color photosensitive material comprising a support, a cyan-coupler containing silver halide photosensitive emulsion layer, a magenta coupler containing silver halide photosensitive emulsion layer, and a yellow coupler containing silver halide photosensitive emulsion layer said material containing a compound represented by the formula:

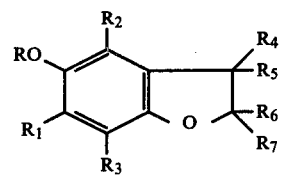

Formula (II)

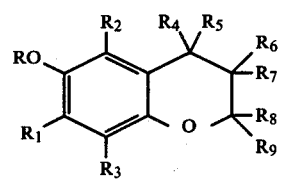

Formula (III)

or

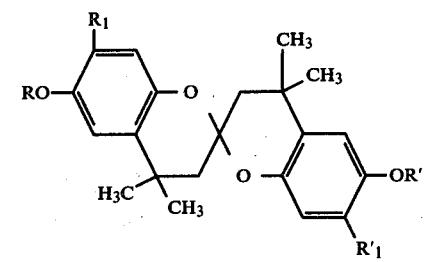

Formula (IV)

wherein R represents an alkyl group, an alkenyl group, a cycloalkyl group, an aryl group or a heterocyclic group selected from piperadine, morpholine, imidazoline, thiazoline, pyridine, pyrimidine, triazine; $R_1$, $R_2$ and $R_3$ individually represent hydrogen, halogen, an alkyl group, an alkylthio group, an alkoxy group, an aryl group, an aryloxy group, an arylthio group, an acyl group, an acylamino group, a diacylamino group, an acyloxy group, a sulfonamido group, an alkylamino group, a cycloalkyl group or an alkoxycarbonyl group; R' is as defined for R; $R'_1$ is as defined for $R_1$; and $R_4$, $R_5$, $R_6$, $R_7$, $R_8$, and $R_9$ individually represent hydrogen, an alkyl group, an alkoxy group, an alkylthio group, an alkenyl group, an alkenyloxy group, an aryl group, an aryloxy group, an N-substituted amino group or a heterocyclic group selected from piperadine, morpholine, imadolizine, thiazoline, pyridine, pyrimidine, triazine; provided that $R_8$ and $R_9$ can cooperatively cyclized to form a cyclohexane ring which may be substituted with alkyl.

3. A color photosensitive material according to claim 1 wherein the photosensitive layer contains the compound.

4. A color photosensitive material according to claim 1 wherein the photosensitive material further comprises a layer adjacent to a hydrophilic layer, the adjacent layer containing the compound.

5. A color photosensitive material according to claim 1 wherein the photosensitive layer contains the compound.

6. A color photosensitive material according to claim 1 wherein the compound is selected from the compounds represented by the formulas (III) and (IV).

7. A color photosensitive material according to claim 6 wherein R in formula (III) is an alkyl group having 8-32 carbon atoms.

8. A color photosensitive material according to claim 7 wherein the alkyl group for R in formula (III) has 12-32 carbon atoms.

9. A color photosensitive material according to claim 6 wherein the compound is represented by formula (IV).

10. A color photosensitive material according to claim 2 wherein at least one of the three emulsion layers contains the compound.

11. A color photosensitive material according to claim 2 wherein at least one of the yellow coupler containing silver halide photosensitive emulsion layer and the cyan coupler containing silver halide photosensitive emulsion layer contains the compound.

12. A color photosensitive material according to claim 2 wherein the compound is selected from the compounds represented by formulas (III) and (IV).

13. A color photosensitive material according to claim 12 wherein R in formula (III) is an alkyl group having 8-32 carbon atoms.

14. A color photosensitive material according to claim 13 wherein the alkyl group for R in formula (III) has 12-32 carbon atoms.

15. A color photosensitive material according to claim 13 wherein the compound is present in the magenta coupler containing silver halide photosensitive emulsion layer.

16. A color photosensitive material according to claim 15 wherein said magenta coupler is selected from the group consisting of
 1-(2,4,6-Trichlorophenyl)-3-(2-chloro-5-octadecylsuccimidoanilino)-5-pyrazolone
 1-(2,4,6-Trichlorophenyl)-3-(2-chloro-5-octadecylcarbamoylanilino)-5-pyrazolone
 1-(2,4,6-Trichlorophenyl)-3-(2-chloro-5-tetradecanamidoanilino)-5-pyrazolone
 1-(2,4,6-Trichlorophenyl)-3-{2-chloro-5-[α-(3-t-butyl-4-hydroxyphenoxy)tetradecanamido]anilino}-5-pyrazolone
 4,4'-Benzylidenebis[1-(2,4,6-trichlorophenyl)-3-{2-chloro-5-[γ-(2,4-di-t-amylphenoxy)-butylamido]anilino}-5-pyrazolone]
 4,4'-Benzylidenebis[1-(2,3,4,5,6-pentachlorophenyl)-3-{2-chloro-5-[γ-(2,4-di-t-amylphenoxy)-butylamido]anilino}-5-pyrazolone]
 1-(2,6-Dichloro-4-methoxyphenyl)-3-(2-methyl-5-acetamidoanilino)-5-pyrazolone
 1-(2-Chloro-4,6-dimethylphenyl)-3-(2-methyl-5-chloroanilino)-5-pyrazolone
 1-(2,4,6-Trichlorophenyl)-3-(4-nitroanilino)-5-pyrazolone
 1-(2,4,6-Trichlorophenyl)-3-(2-chloro-5-octadecenylsuccimidoanilino)-5-pyrazolone.
 1-(2,4,6-Trichlorophenyl)-3-(2-chloro-5-tridecanamidoanilino)-5-pyrazolone.

17. A color photosensitive material according to claim 12 wherein the compound is represented by formula (IV).

* * * * *